US008071315B2

(12) United States Patent
Reed et al.

(10) Patent No.: US 8,071,315 B2
(45) Date of Patent: Dec. 6, 2011

(54) DETECTING BCL-B EXPRESSION IN CANCER AND USES THEREOF

(75) Inventors: John C. Reed, Rancho Santa Fe, CA (US); Maryla Krajewska, Oceanside, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 12/433,481

(22) Filed: Apr. 30, 2009

(65) Prior Publication Data

US 2009/0275040 A1 Nov. 5, 2009

Related U.S. Application Data

(60) Provisional application No. 61/048,995, filed on Apr. 30, 2008.

(51) Int. Cl.
*G01N 33/53* (2006.01)
(52) U.S. Cl. ........................................ 435/7.1
(58) Field of Classification Search ................ None
See application file for complete search history.

(56) References Cited

PUBLICATIONS

Tockman et al (Cancer Res., 1992, 52:2711s-2718s).*
Bivona et al, PKC regulates a farnesyl-electrostatic switch on K-Ras that promotes its association with Bcl-XL on mitochondria and induces apoptosis, Mol Cell, 21, 481-93 (2006).
Chao et al, Bcl-2 family: regulators of cell death, Annu Rev Immunol, 16, 395-419 (1998).
Chauhan et al, A novel Bcl-2/Bcl-X(L)/Bcl-w inhibitor ABT-737 as therapy in multiple myeloma, Oncogene (2006).
Cheng et al, Conversion of Bcl-2 to a Bax-like death effector by caspases, Science, 278, 1966-8 (1997).
Cheng et al, Mitochondrial factors with dual roles in death and survival, Oncogene, 25, 4697-705 (2006).
Clem et al, Modulation of cell death by Bcl-XL through caspase interaction, Proc Natl Acad Sci USA 95, 554-9 (1998).
Elsaleh, The microsatellite instability phenotype in human colorectal carcinoma: relationship to sex, age, and tumor site, Gastroenterology, 121, 230-1 (2001).
Hanahan et al., The hallmarks of cancer, Cell, 121, 57-70 (2000).
Hans et al, Confirmation of the molecular classification of diffuse large B-cell lymphoma by immunohistochemistry using a tissue microarray, Blood, 103, 275-82 (2004).
Inohara et al, Diva, a Bcl-2 homologue that binds directly to Apaf-1 and induces BH3-independent cell death, J Biol Chem, 273, 32479-86 (1998).
Ke et al, A novel Bcl-2 family member that differentially binds and regulates Bax and Bak, 276, 12481-4 (2001).
Krajewska et al, Analysis of apoptosis protein expression in early-stage colorectal cancer suggests opportunities for new prognostic biomarkers, Clin Cancer Res, 11, 5451-61 (2005a).
Krajewska et al, Claudin-1 immunohistochemistry for distinguishing malignant from benign epithelial lesions of prostate, Prostate, 67, 907-10 (2007).
Krajewska et al, Elevated expression of inhibitor of apoptosis proteins in prostate cancer, Clin Cancer Res, 9, 4914-25 (2003).
Krajewska et al, Expression of Bcl-2 family member Bid in normal and malignant tissues, Neoplasia, 4, 129-40 (2002).
Krajewska et al, Tumor-associated alterations in caspase-14 expression in epithelial malignancies, Clin Cancer Res, 11, 5462-71 (2005b).
Krajewski et al, Detection of multiple antigens on Western blots, Anal Biochem, 236, 221-8 (1996).
Krajewski et al, Immunohistochemical analysis of Mcl-1 protein in human tissues: differential regulation of Mcl-1 and Bcl-2 protein production suggests a unique role for Mcl-1 in control of programmed cell death in vivo, Am J. Pathol, 146, 1309-19 (1995).
Krajewski et al, Release of caspase-9 from mitochondria during neuronal apoptosis and cerebral ischemia, Proc Natl Acad Sci USA, 96, 5752-7 (1999).
Le Gouill et al, Mcl-1 regulation and its role in multiple myeloma, Cell Cycle, 3, 1259-62 (2004).
Lin et al, Conversion of Bcl-2 from protector to killer by interaction with nuclear orphan receptor TR3/NGFI-B/Nur77, Cell, 116, 527-40 (2004).
Luciano et al, Nur77 converts phenotype of Bcl-B, an antiapoptotic protein expressed in plasma cells and myeloma, Blood, 109, 3849-55 (2007).
Manz et al, Immunological memory stabilizing autoreactivity, Curr Top Microbiol Immunol, 305, 241-57 (2006).
Meinhold-Heerlein et al, Expression and potential role of Fas-associated phosphatase-1 (FAP-1) in ovarian cancer, Amer J Pathol, 158, 1335-44 (2001).
Oancea et al, Apoptosis of multiple myeloma, Int J Hematol, 80, 224-31 (2004).
Radbruch et al, Competence and competition: the challenge of becoming a long-lived plasma cell, Nat Rev Immunol, 6, 741-50 (2006).
Reed et al., Mechanisms of apoptosis (Warner/Lambert Award), Amer J. Pathol, 157, 1415-30 (2000).
Ruifrok et al, Quantification of histochemical staining by color deconvolution, Anal Quant Cytol Histol, 23, 291-9 (2001).
Shapiro-Shelef et al, Blimp-1 is required for maintenance of long-lived plasma cells in the bone marrow, J Exp Med, 202, 1471-6 (2005).
Shapiro-Shelef et al, Regulation of plasma-cell development, Nat Rev Immunol, 5, 230-42 (2005).
Song et al, Boo, a novel negative regulator of cell death, interactst with Apaf-I , EMBO, 18, 167-78 (1998).
Wang et al, Mechanisms of Bcl-2 protein function, Histol Histopathol, 13, 521-30 (1998).
Went et al, Plasma cell quantification in bone marrow by computer-assisted image analysis, Histol Histopathol, 21, 951-6 (2006).
Zhai et al, Comparison of chemical inhibitors of antiapoptotic Bcl-2-family proteins, Cell Death Differ, 13, 1419-21 (2006).
Zhang et al, Bc12-K-I 0, a novel anti-apoptotic member of the Bcl-2 family, blocks apoptosis in the mitochondria death pathway but not in the death receptor pathway, Hum Mol Genet, 10, 2329-39 (2001).
Reed et al., Mechanisms of Bcl-2 family protein function and dysfunction in health and disease, Behring Inst Mitt, 97, 72-100 (1996) part 1.
Reed et al., Mechanisms of Bcl-2 family protein function and dysfunction in health and disease, Behring Inst Mitt, 97, 72-100 (1996) part 2.

* cited by examiner

*Primary Examiner* — Sean Aeder
(74) *Attorney, Agent, or Firm* — Pabst Patent Group LLC

(57) ABSTRACT

Provided herein are compositions and methods of detecting Bcl-B expression in cancer cells to prognose, monitor, or select therapies for cancers such as breast cancer, prostate cancer, lung cancer, or gastric cancer.

9 Claims, 14 Drawing Sheets

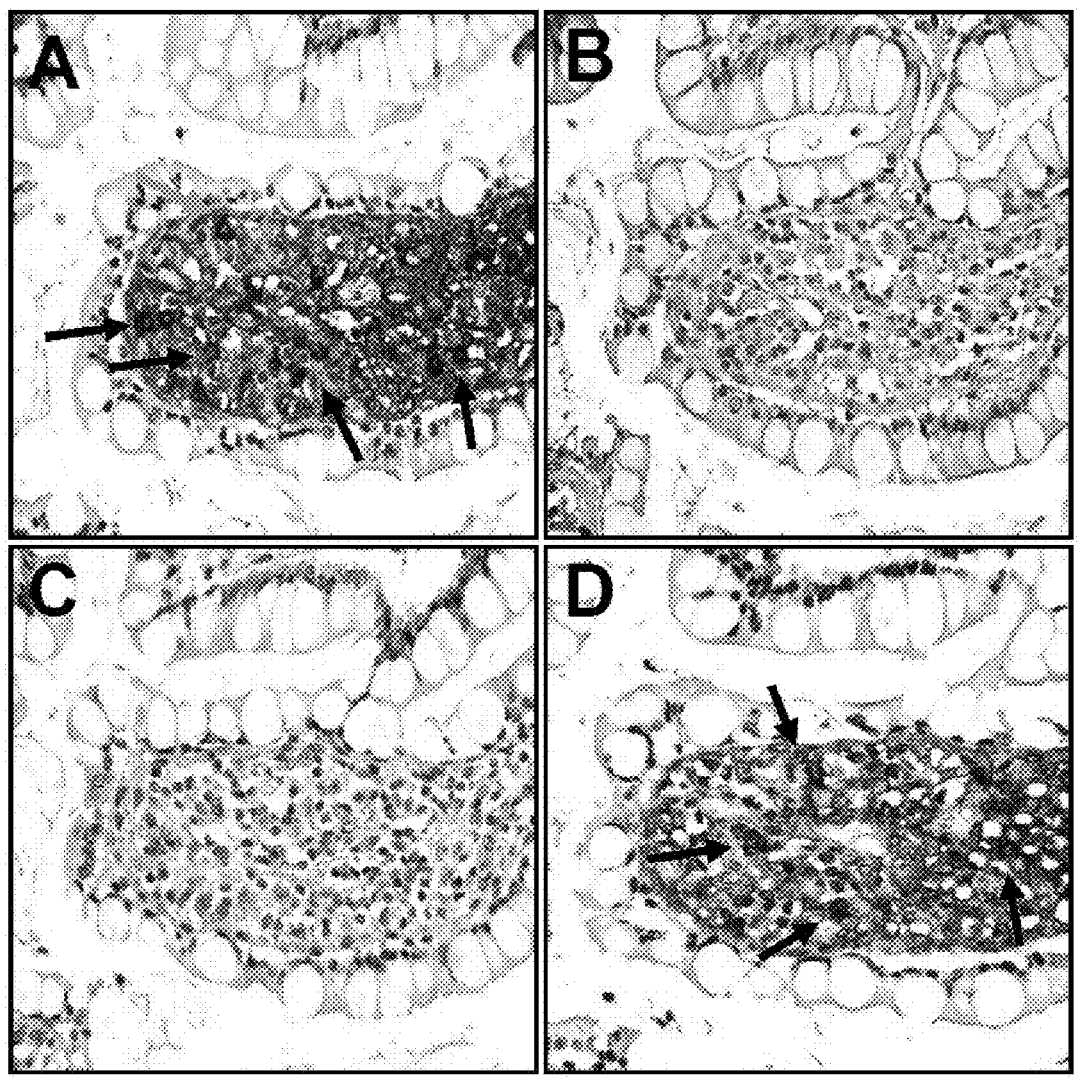
FIG. 7A-D

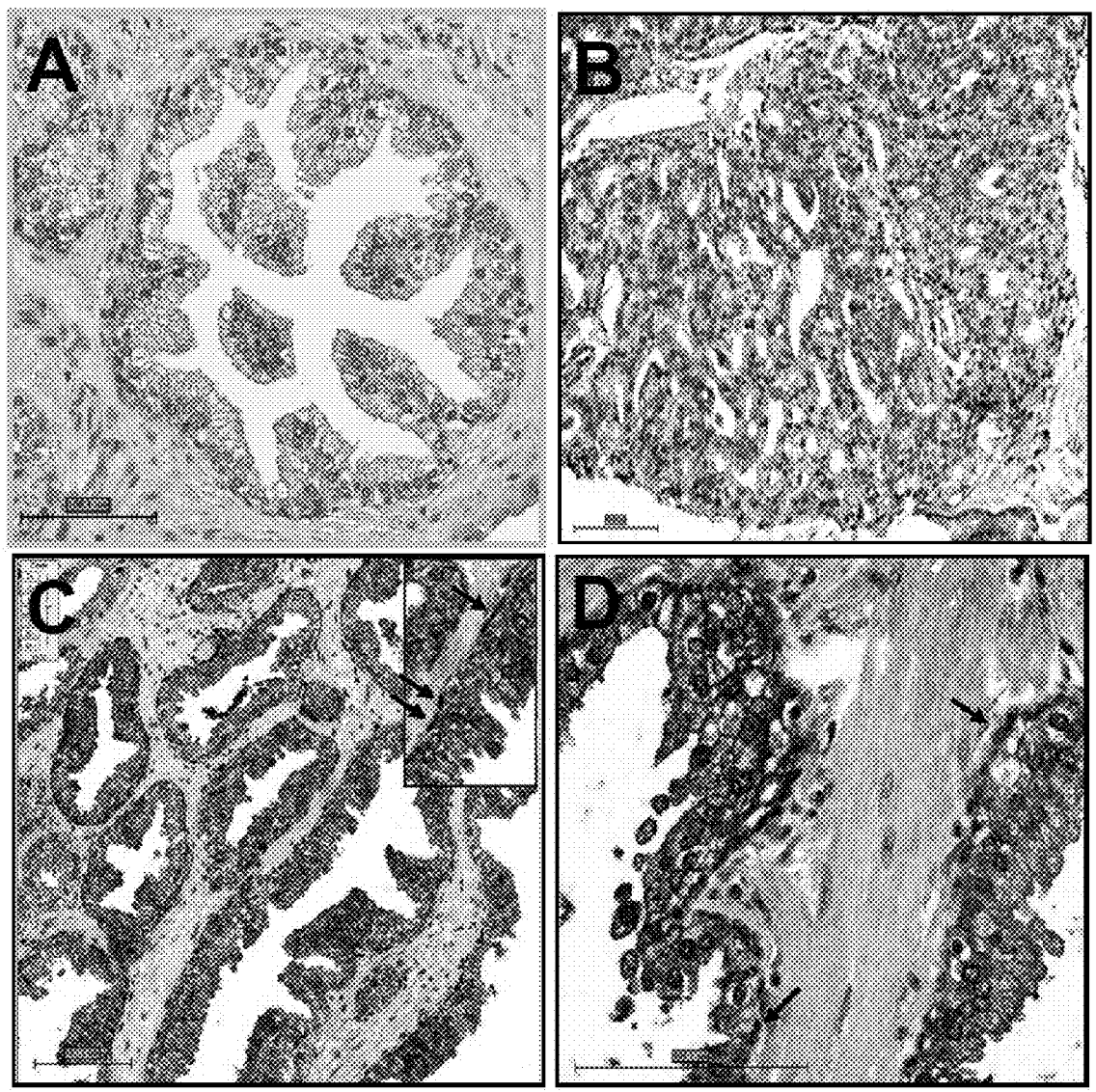
FIG. 8A-D

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: Synthetic peptide corresponding to residues 32-
      50 of human Bcl-B
<220> FEATURE:
<221> NAME/KEY: UNSURE
<222> LOCATION: (1)..(19)

<400> SEQUENCE: 1

Arg Glu Pro Gly Thr Pro Glu Pro Ala Pro Ser Thr Pro Glu Ala Ala
1               5                  10                  15

Val Leu Arg

<210> SEQ ID NO 2
<211> LENGTH: 615
<212> TYPE: DNA
<213> ORGANISM: Homo sapiens
<220> FEATURE:
<221> NAME/KEY: gene
<222> LOCATION: (1)..(615)

<400> SEQUENCE: 2
atggttgacc agttgcggga gcgcaccacc atggccgacc cgctgcggga gcgcaccgag      60
ctgttgctgg ccgactacct ggggtactgc gcccgggaac ccggcacccc cgagccggcg     120
ccatccacgc ccgaggccgc cgtgctgcgc tccgcggccg ccaggttacg gcagattcac     180
cggtcctttt tctccgccta cctcggctac cccgggaacc gcttcgagct ggtggcgctg     240 atgcggatt ccgtgctctc cgacagcccc ggccccacct ggggcagagt ggtgacgctc      300
gtgaccttcg cagggacgct gctggagaga gggccgctgg tgaccgcccg gtggaagaag     360
tggggcttcc agccgcggct aaaggagcag gagggcgacg tcgcccggga ctgccagcgc     420
ctggtggcct tgctgagctc gcggctcatg gggcagcacc gcgcctggct gcaggctcag     480
ggcggctggg atggcttttg tcacttcttc aggaccccct tccactggc ttttggaga      540 aaacagctgg tccaggcttt tctgtcatgc ttgttaacaa cagccttcat ttatctctgg     600
```

-continued

```
acacgattat tatga                                                615

<210> SEQ ID NO 3
<211> LENGTH: 204
<212> TYPE: PRT
<213> ORGANISM: HOMO SAPIEN
<220> FEATURE:
<221> NAME/KEY: UNSURE
<222> LOCATION: (1)..(204)

<400> SEQUENCE: 3

Met Val Asp Gln Leu Arg Glu Arg Thr Thr Met Ala Asp Pro Leu Arg
1               5                   10                  15

Glu Arg Thr Glu Leu Leu Leu Ala Asp Tyr Leu Gly Tyr Cys Ala Arg
            20                  25                  30

Glu Pro Gly Thr Pro Glu Pro Ala Pro Ser Thr Pro Glu Ala Ala Val
        35                  40                  45

Leu Arg Ser Ala Ala Ala Arg Leu Arg Gln Ile His Arg Ser Phe Phe
    50                  55                  60

Ser Ala Tyr Leu Gly Tyr Pro Gly Asn Arg Phe Glu Leu Val Ala Leu
65                  70                  75                  80

Met Ala Asp Ser Val Leu Ser Asp Ser Pro Gly Pro Thr Trp Gly Arg
                85                  90                  95

Val Val Thr Leu Val Thr Phe Ala Gly Thr Leu Leu Glu Arg Gly Pro
            100                 105                 110

Leu Val Thr Ala Arg Trp Lys Lys Trp Gly Phe Gln Pro Arg Leu Lys
            115                 120                 125

Glu Gln Glu Gly Asp Val Ala Arg Asp Cys Gln Arg Leu Val Ala Leu
    130                 135                 140

Leu Ser Ser Arg Leu Met Gly Gln His Arg Ala Trp Leu Gln Ala Gln
145                 150                 155                 160

Gly Gly Trp Asp Gly Phe Cys His Phe Phe Arg Thr Pro Phe Pro Leu
                165                 170                 175

Ala Phe Trp Arg Lys Gln Leu Val Gln Ala Phe Leu Ser Cys Leu Leu
            180                 185                 190

Thr Thr Ala Phe Ile Tyr Leu Trp Thr Arg Leu Leu
            195                 200
```

DETECTING BCL-B EXPRESSION IN CANCER AND USES THEREOF

CROSS-REFERENCE TO RELATED APPLICATIONS

This application claims benefit of U.S. Provisional Application No. 61/048,995, filed Apr. 30, 2008. Application No. 61/048,995, filed Apr. 30, 2008, is hereby incorporated herein by reference in its entirety.

STATEMENT REGARDING FEDERALLY SPONSORED RESEARCH

This invention was made with government support under Grant CA-113318, GM-60554, CA-81534, P30CA06055, and CA114810 awarded by the National Institutes of Health. The government has certain rights in the invention.

BACKGROUND

Defective apoptosis represents one of the six recognized cardinal features of cancer (Hanahan D, et al. 2000). Bcl-2-family proteins are evolutionarily conserved regulators of cell life and death. In humans, six anti-apoptotic members of the Bcl-2 family have been identified, including Bcl-2, BCl-$X_L$, Mcl-1, Bcl-W, Bfl-1, and Bcl-B (Reed J C. 2000). Over-expression of Bcl-2 and some other anti-apoptotic members of the Bcl-2 family has been documented in human cancers (Reed J C. 1996). Given that investigational therapies targeting specific Bcl-2-family proteins or their encoding mRNAs are now in clinical trials, it is important to define which Bcl-2 family proteins are over-expressed in various types of cancer, so that appropriate targeted therapies can be matched to specific malignancies.

BRIEF SUMMARY

In accordance with the purpose of this invention, as embodied and broadly described herein, this invention relates to compositions and methods of detecting Bcl-B expression to prognose, monitor, or select therapies for cancers.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows GST fusion proteins containing Bcl-XL, Bfl-1, Bcl-2, Mcl-1, Bcl-W, and Bcl-B (0.1 µg/lane) analyzed by immunoblotting using AR-77 antiserum (top). The blot was reprobed with anti-GST (bottom). Cell lysates from HeLa cells with tetracycline-inducible Bcl-B are also included (tet on/off). FIGS. 1B and 1C show selected GST-fusion proteins (0.05 µg/lane) and human tissue lysates normalized for total protein content (50 µg/lane) subjected to SDS-PAGE/immunoblot analysis, using AR-77 [1:2,000 (v/v) (B) or BR-49 [1:3,000 (v/v)] (C) antibodies to Bcl-B (top). Blots were reprobed with anti-HSP60 and anti-β-actin antibodies (bottom). Antibody detection was accomplished using an enhanced chemiluminescence method. Black arrows indicated Bcl-B momers or SDS-resistant Bcl-B dimers. White arrows indicate GST-Bcl-B fusion protein.

FIGS. 2A-2D show serial sections of normal human lymph node specimen stained with (A) anti-Bcl-B antiserum (raised against recombinant Bcl-B protein) (400×), (B) preimmune serum (100×), (C) anti-Bcl-B antiserum preabsorbed with GST-Bcl-B (200×), and (D) anti-Bcl-B antiserum preabsorbed with GST-Bcl-xL (200×). Specimens were counterstained with hematoxylin. FIGS. 2E-2H show human lymph node (E-F) and spleen (G-H) sections containing secondary follicles (E, H) stained with the Bcl-B antibody to visualize immunopositive B cells in germinal centers (E, H) and plasma cells in medullary cords (F) and red pulp (G). Photomicrographs were taken at original magnifications ranging from 100× to 400×. FIGS. 2I-2L show TMA containing gut specimens from patients with Crohn's disease were double stained with the Bcl-B (DAB, brown) and CD 138 (SG, black) antibodies and counterstained with Nuclear Red. The brown (I) and black (J) colors were separated in the annotated regions using a color deconvolution algorithm (Aperio). Quantification of immunohistochemical staining for Bcl-B (K) and CD 138 (L) was performed using color translation and an automated thresholding algorithm (Aperio). Shown is colocalization of Bcl-B and CD138 cells. Original magnifications are 100× (I, J) and 400× (K, L).

and poorly (P) differentiated gastric cancers (panel E). The mean immunopercentage/immunoscore is plotted as a marker; whiskers reflect ±1.96 SE from the mean. FIG. 5F shows Bcl-B immunopercentage data for SCLC dichotomized into high versus low expression groups based on the median values. The percentage of patients remaining alive (ordinate) was compounded over time (abscissa) (in years), by the Kaplan-Meier method. The log-rank test was used for correlating the immunostaining data with the patient survival.

FIG. 6A shows immunoblot data for (1) recombinant His6-Bcl-GL; (2) recombinant GST-Bcl-B, showing bands corresponding to Bcl-B, GST-Bcl-B, dimers and oligomers of these proteins; and (C) plasma cell specimen. FIG. 6B shows immunoblot data for (1) GST-Bcl-B protein, (2-4) plasma cell preparations from normal bone marrow; and (5) plasma cells isolated from multiple myeloma bone marrow specimen. FIG. 6C shows immunoblot data for (1) plasma cell preparation from normal bone marrow and (2) plasma cells isolated from multiple myeloma bone marrow specimen. Unmodified Bcl-B (arrow head) and modified (possibly ubiquitinylated) or SDS-resistant oligomerized forms of Bcl-B protein are seen.

FIGS. 7A-7D show immunohistochemical analysis of Bcl-B immunoreactivity in plasma cells. Serial sections of a specimen of colon from a patient with Crohn's disease were stained with (A) anti-Bcl-B antiserum (AR-77), (B) preimmune serum, (C) anti-Bcl-B antiserum preadsorbed with GST-Bcl-B, and (D) anti-Bcl-B antiserum preadsorbed with GST-Bcl-XL proteins. Antibody detection was accomplished with diaminobenzidine, followed by hematoxylin counterstaining of nuclei (400× original magnification). Note that the AR-77 anti-Bcl-B antiserum stains plasma cells (arrows highlight some examples) and that Bcl-B protein preadsorption neutralizes staining, unlike Bcl-XL preadsorption.

FIGS. 8A-8D show Bcl-B expression in secretory cells of prostate gland. Prostate tissue speciments (A—Normal gland; B—Adenocarcinoma; C-D—BPH) were stained with anti-Bcl-B antiserum. Antibody detection was with diaminobenzidine, followed by hematoxylin counterstaining of nuclei. Shown are various magnifications (length bars=micrometers), including an inset with higher magnification in (C). Note that luminal secretory cells are weakly (normal gland) or strongly (BPH) stained, while basal cells show no staining (arrows).

DETAILED DESCRIPTION

Figure 1A:
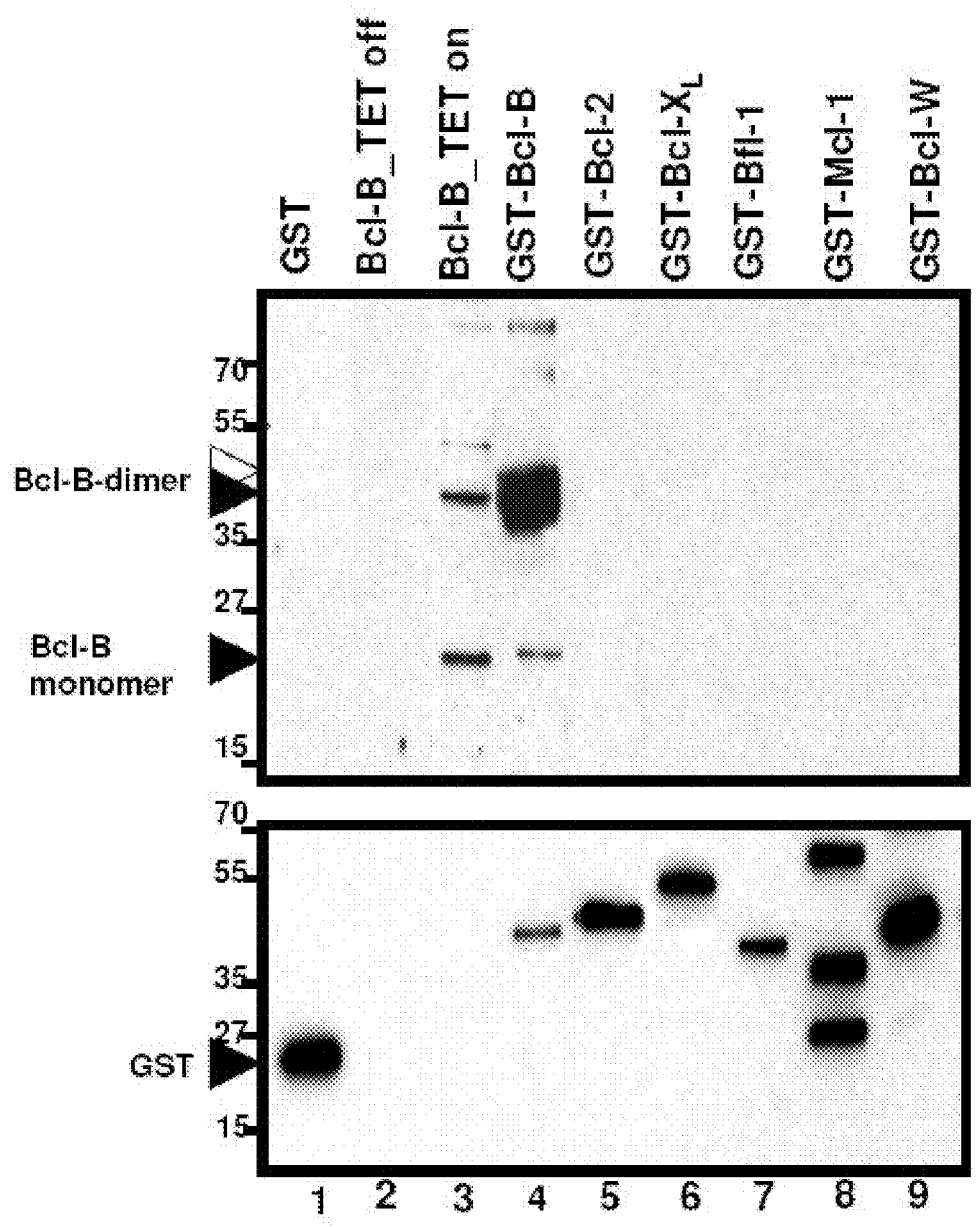
FIGS. 1A, 1B, and 1C show characterization of Bcl-B antibodies and immunodetection of Bcl-B protein in human tissue lysates.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an antibody is disclosed and discussed and a number of modifications that can be made to a number of molecules including the antibody are discussed, each and every combination and permutation of antibody and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. General

Provided herein are methods relating to examining the expression of Bcl-B in one or more cells of a cancer, such as breast cancer, prostate cancer, lung cancer, or gastric cancer.

Bcl-B (a.k.a. Bcl2-L-10) was the last anti-apoptotic member of the human Bcl-2 family to be identified (Ke N, et al. 2001; Zhang H, et al. 2001). Bcl-B contains conserved BH1, BH2, BH3-like, and BH4 domains, as well as a C-terminal transmembrane domain, typical of anti-apoptotic Bcl-2-family proteins that target intracellular membranes of mitochondria (Ke N, et al. 2001; Zhang H, et al. 2001). Dimerization of pro- and anti-apoptotic Bcl-2-family proteins plays an important role in controlling their activity (Chao D T, et al. 1998; Wang H-G, et al. 1998). The Bcl-B protein was shown to differentially bind pro-apoptotic Bcl-2-family members (Ke N, et al. 2001). Thus, Bcl-B can have a unique pattern of selectivity for binding to various pro-apoptotic members of the Bcl-2 family, indicating a specific role for this protein in controlling cell life and death.

Though initially recognized for its anti-apoptotic activity, the mouse ortholog of Bcl-B reportedly displays either anti-apoptotic or pro-apoptotic activity, depending on cellular context (Inohara N, et al. 1998; Song Q, et al. 1999). Bcl-B binds orphan nuclear receptor Nur77/TR3, which converts the phenotype of Bcl-B from anti-apoptotic to pro-apoptotic (Luciano F, et al. 2007). Thus, Bcl-B is similar to Bcl-2 in its ability to display opposing effects on apoptosis, based on protein interactions and other factors (Lin B, et al. 2004).

Bcl-B protein expression was investigated in normal human tissues and in several types of human malignancy by immunohistochemistry using monospecific antibodies that recognize Bcl-B and the expression results correlated with clinically relevant variables.

Provided herein is a method of determining the severity of a breast cancer, prostate cancer, or lung cancer comprising examining the expression of Bcl-B in one or more cells of said cancer. In some aspects, an increase in the relative amount of Bcl-B expression in the cancer cells or as compared to that of normal reference cells indicates an increase in cancer severity. In some aspects of the method an increase in the amount of Bcl-B expression in the cancer cells or an increase in the number or percentage of cells with detectable Bcl-B expression as compared to that of normal reference cells indicates a higher tumor grade. In some aspects of the method an increase in the amount of Bcl-B expression in the cancer cells or an increase in the number or percentage of cells with detectable Bcl-B expression as compared to that of normal reference cells indicates a greater likelihood of death. In some aspects of the method an increase in the amount of Bcl-B expression in the cancer cells or an increase in the number or percentage of cells with detectable Bcl-B expression as compared to that of normal reference cells indicates metastasis. In some aspects, an increase in the amount of Bcl-B expression in the breast, prostate or lung cancer cells or an increase in the number or percentage of breast, prostate or lung cells with detectable Bcl-B expression as compared to that of normal reference cells indicates an increase in cancer severity. In some aspects of the method an increase in the amount of Bcl-B expression in the breast, prostate of lung cancer cells or an increase in the number or percentage of breast, prostate or lung cells with detectable Bcl-B expression as compared to that of normal reference cells indicates a higher tumor grade. In some aspects of the method an increase in the amount of Bcl-B expression in the breast, prostate or lung cancer cells or an increase in the number or percentage of breast, prostate or lung cells with detectable Bcl-B expression as compared to that of normal reference cells indicates a greater likelihood of death. In some aspects of the method an increase in the amount of Bcl-B expression in the breast, prostate or lung cancer cells or an increase in the number or percentage of breast, prostate or lung cells with detectable Bcl-B expression as compared to that of normal reference cells indicates metastasis.

Also provided herein is a method of determining the severity of a gastric cancer comprising examining the expression of Bcl-B in one or more cells of said cancer. In some aspects of the method a decrease in the amount of Bcl-B expression in the cancer cells or a decline in the number or percentage of cells with detectable Bcl-B expression as compared to that of normal reference cells indicates an increase in cancer severity. In some aspects of the method a decrease in the amount of Bcl-B expression in the cancer cells or a decline in the number or percentage of cells with detectable Bcl-B expression as compared to that of normal reference cells indicates a higher tumor grade. In some aspects of the method a decrease in the amount of Bcl-B expression in the cancer cells or a decline in the number or percentage of cells with detectable Bcl-B expression as compared to that of normal reference cells indicates a greater likelihood of death. In some aspects of the method a decrease in the amount of Bcl-B expression in the cancer cells or a decline in the number or percentage of cells with detectable Bcl-B expression as compared to that of normal reference cells indicates metastasis. In some aspects of the method a decrease in the amount of Bcl-B expression in the gastric cancer cells or a decline in the number or percentage of gastric cells with detectable Bcl-B expression as compared to that of normal reference cells indicates an increase in cancer severity. In some aspects of the method a decrease in the amount of Bcl-B expression in the gastric cancer cells or a decline in the number or percentage of gastric cells with detectable Bcl-B expression as compared to that of normal reference cells indicates a higher tumor grade. In some aspects of the method a decrease in the amount of Bcl-B expression in the gastric cancer cells or a decline in the number or percentage of gastric cells with detectable Bcl-B expression as compared to that of normal reference cells indicates a greater likelihood of death. In some aspects of the method a decrease in the amount of Bcl-B expression in the gastric cancer cells or a decline in the number or percentage of gastric cells with detectable Bcl-B expression as compared to that of normal reference cells indicates metastasis.

Disclosed herein is a method of monitoring the progression of a breast cancer, prostate cancer, or lung cancer comprising examining the expression of Bcl-B in one or more cells of said cancer. In some aspects, an increase in the amount of Bcl-B expression in the cancer cells or an increase in the number or percentage of cells with detectable Bcl-B expression as compared to that of normal reference cells indicates an increased risk of cancer progression. In some aspects, an increase in the amount of Bcl-B expression in the breast, prostate or lung cancer cells or an increase in the number or percentage of breast, prostate or lung cells with detectable Bcl-B expression as compared to that of normal reference cells indicates an increased risk of cancer progression.

Also disclosed herein is a method of monitoring the progression of a gastric cancer, comprising examining the expression of Bcl-B in one or more cells of said cancer. In some aspects, a decrease in the amount of Bcl-B expression in the cancer cells or a decrease in the number or percentage of cells with detectable Bcl-B expression as compared to that of normal reference cells indicates an increased risk of cancer progression. In some aspects, a decrease in the amount of Bcl-B expression in the gastric cancer cells or a decrease in the number or percentage of gastric cells with detectable Bcl-B expression as compared to that of normal reference cells indicates an increased risk of cancer progression.

Reference herein to an increase in the amount of Bcl-B expression or to an increase in the number or percentage of cells with detectable Bcl-B includes an at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200% increase as compared to that of normal reference cells.

Reference herein to an decrease in the amount of Bcl-B expression or to an decrease in the number or percentage of cells with detectable Bcl-B includes an at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200% decrease as compared to that of normal reference cells.

Also disclosed herein is a method of selecting a therapy for treating a subject with breast cancer or prostate cancer, comprising examining the expression of Bcl-B in one or more cells of said cancer. In this regard, it has been controversial how to optimally treat patients with early stage (stage I/II) prostate and breast cancer, because staging methods do not detect micrometastatic disease. If tumor cells have not yet acquired metastatic competency, then local/regional therapy can be effective (e.g., surgery, radiotherapy). However, if tumor cells have already metastasized, then the patient should receive systemic therapy, such as chemotherapy or anti-hormonal therapy. Testing for Bcl-B can discriminate those patients at risk of having tumor micrometastaces and those who need systemic therapy.

Accordingly, in some aspects, a higher amount of Bcl-B expression in the cancer cells or a higher number or percentage of cancer cells with detectable Bcl-B expression as compared to that of non-metastatic and/or non-neoplastic reference cells indicates that the selected treatment is a systemic therapy. For example, a higher amount of Bcl-B expression in the breast or prostate cancer cells or a higher number or percentage of breast or prostate cancer cells with detectable Bcl-B expression as compared to that of non-metastatic and/or non-neoplastic reference cells can indicate that the selected treatment is adjuvant chemotherapy, hormonal therapy, or a combination thereof. Other systemic therapies are known in the art and can be selected by the physician for use in the disclosed method.

In some aspects, a lower or equivalent amount of Bcl-B expression in the cancer cells or a lower or equivalent number or percentage of cancer cells with detectable Bcl-B expression as compared to that of non-metastatic and/or non-neoplastic reference cells indicates that the selected treatment is a local, regional, or targeted therapy. For example, a lower or equivalent amount of Bcl-B expression in the breast or prostate cancer cells or a lower or equivalent number or percentage of breast or prostate cancer cells with detectable Bcl-B expression as compared to that of non-metastatic and/or non-neoplastic reference cells can indicate that the selected treatment is surgery, local therapy, or a combination thereof. Other targeted therapies, such as anti-angiogenesis therapy, are known in the art and can be selected by the physician for use in the disclosed method.

Also disclosed herein is a method of selecting a therapy for treating a subject with lung cancer, comprising examining the expression of Bcl-B in one or more cells of said cancer, wherein a higher amount of Bcl-B expression in the cancer cells or a higher number or percentage of cancer cells with detectable Bcl-B expression as compared to that of non-metastatic and/or non-neoplastic reference cells indicates that the selected treatment is aggressive chemotherapy, investigational drugs, or a combination thereof.

Reference herein a higher amount of Bcl-B expression or to a higher number or percentage of cells with detectable Bcl-B includes at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200% higher as compared to that of normal reference cells.

Reference herein a lower amount of Bcl-B expression or to a lower number or percentage of cells with detectable Bcl-B includes at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200% lower as compared to that of normal reference cells.

As used herein, "normal reference cells" can refer to healthy cells from the same tissue of the subject as the cancer cells. Alternatively, normal reference cells can refer to non-cancerous cells of similar tissue from one or more unrelated individuals.

As used herein, "non-metastatic reference cells" can refer to primary cancer cells from the subject. Alternatively, non-metastatic reference cells can refer to primary cancer cells of a histologically similar cancer from one or more unrelated individuals.

In some aspects, it is not necessary to measure Bcl-B expression in normal (non-neoplastic) reference cells or non-metastatic reference cells to practice the methods. In these aspects, it is sufficient to compare the amount, number, or percentage identified for the cancer cells of the subject to an amount, number, or percentage documented for the normal (non-neoplastic) reference cells or non-metastatic reference cells.

The amount of Bcl-B expression in the cancer cells or the number, or percentage of cells with detectable Bcl-B expression can be evaluated or measured using standard methods known in the art, including those disclosed herein. For example, Bcl-B expression can be detected using immunoassays or nucleic acid detection methods. The number or percentage of cells with detectable Bcl-B expression can be evaluated, for example, using cell separation methods.

1. Breast Cancer

The tumor of the disclosed method can be a breast cancer. Thus, the breast tumor can be ductal carcinoma in situ (DCIS), lobular carcinoma in situ (LCIS), infiltrating ductal carcinoma (IDC), infiltrating lobular carcinoma (ILC), medullary carcinoma, inflammatory breast cancer (IBC), tubular carcinoma (TC), colloid carcinoma, metaplastic carcinoma, papillary carcinoma, adenoid cystic carcinoma (ACC), secretory carcinoma, or Paget's disease of the breast. The breast tumor can be estrogen receptor-negative, progesterone receptor-negative, and HER2-negative (triple-negative breast cancer).

Breast cancers are described along four different classification schemes, or groups, each based on different criteria and serving a different purpose: pathology, grade of tumor, protein & gene expression status, and stage of a tumor.

A pathologist can categorize each tumor based on its histological (microscopic anatomy) appearance and other criteria. The most common pathologic types of breast cancer are invasive ductal carcinoma, malignant cancer in the breast's ducts, and invasive lobular carcinoma, malignant cancer in the breast's lobules. The histological grade of a tumor is determined by a pathologist under a microscope. A well-differentiated (low grade) tumor resembles normal tissue. A poorly differentiated (high grade) tumor is composed of disorganized cells and, therefore, does not look like normal tissue. Moderately differentiated (intermediate grade) tumors are somewhere in between.

Breast cancers can be tested for expression, or detectable effect, of the estrogen receptor (ER), progesterone receptor (PR) and HER2/neu proteins. These tests can be done by immunohistochemistry. The profile of expression of a given tumor helps predict its prognosis, or outlook, and helps an oncologist choose the most appropriate treatment. As disclosed herein, the amount of Bcl-B expression in the cancer cells or the number, or percentage of cells with detectable Bcl-B expression can further be used to predict the prognosis and guide the oncologist to choose the most appropriate treatment.

The currently accepted staging scheme for breast cancer is the TNM classification: Tumor, lymph Node, and Metastases. There are five tumor classification values (Tis, T1, T2, T3 or T4) which depend on the presence or absence of invasive cancer, the dimensions of the invasive cancer, and the presence or absence of invasion outside of the breast (e.g. to the skin of the breast, to the muscle or to the rib cage underneath). There are four lymph node classification values (N0, N1, N2 or N3) which depend on the number, size and location of breast cancer cell deposits in lymph nodes. There are two metastatic classification values (M0 or M1) which depend on the presence or absence of breast cancer cells in locations other than the breast and lymph nodes (so-called distant metastases, e.g. to bone, brain, lung).

Breast cancer is diagnosed by the examination of surgically removed breast tissue. A number of procedures can obtain tissue or cells prior to definitive treatment for histological or cytological examination. Such procedures include fine-needle aspiration, nipple aspirates, ductal lavage, core needle biopsy, and local surgical excision. These diagnostic steps, when coupled with radiographic imaging, are usually accurate in diagnosing a breast lesion as cancer. Occasionally, pre-surgical procedures such as fine needle aspirate may not yield enough tissue to make a diagnosis, or may miss the cancer entirely. Imaging tests are sometimes used to detect metastasis and include chest X-ray, bone scan, Cat scan, MRI, and PET scanning. While imaging studies are useful in determining the presence of metastatic disease, they are not in and of themselves diagnostic of cancer. Only microscopic evaluation of a biopsy specimen can yield a cancer diagnosis. Ca 15.3 (carbohydrate antigen 15.3, epithelial mucin) is a tumor marker determined in blood which can be used to follow disease activity over time after definitive treatment. Blood tumor marker testing is not routinely performed for the screening of breast cancer, and has poor performance characteristics for this purpose.

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided to high risk and low risk cases, with each risk category following different rules for therapy. Treatment possibilities include radiation therapy, chemotherapy, hormone therapy, and immune therapy.

Radiation has dramatically altered the management of primary breast cancer. Breast conservation, using lumpectomy and radiation therapy, is the treatment of choice in early-stage breast cancer. Cosmetic results are good in most patients, and survival is not compromised. Many patients with locally advanced breast cancer show improvement in local control with radiotherapy, and there is increased survival following radiation. The disclosed methods can be used to guide the selection of the appropriate therapy.

2. Prostate Cancer

Prostate cancer is most often discovered by physical examination or by screening blood tests, such as the PSA (prostate specific antigen) test. There is some current concern about the accuracy of the PSA test and its usefulness. Suspected prostate cancer is typically confirmed by removing a piece of the prostate (biopsy) and examining it under a microscope. Further tests, such as X-rays and bone scans, can be performed to determine whether prostate cancer has spread.

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life. The disclosed methods can be used to guide the selection of the appropriate therapy.

The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy, a urologist obtains tissue samples from the prostate via the rectum. The tissue samples are then examined under a microscope to determine whether cancer cells are present, and to evaluate the microscopic features (or Gleason score) of any cancer found. Tissue samples can be stained for the presence of PSA and other tumor markers in order to determine the origin of malignant cells that have metastasized.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastasize.

After a prostate biopsy, a pathologist identifies the grade of the tumor. The Gleason system can be used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Treatment for prostate cancer can involve watchful waiting, surgery, radiation therapy, High Intensity Focused Ultrasound (HIFU), chemotherapy, cryosurgery, hormonal therapy, or some combination. Which option is generally decided based on the stage of the disease, the Gleason score, and the PSA level. The disclosed methods can be used to further discriminate between therapeutic options based on Bcl-B expression.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy can also be offered if initial treatment fails and the cancer progresses.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, or Bcl-B expression as disclosed herein).

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radiation therapy (radiotherapy), can be used to treat all stages of prostate cancer, or when surgery fails. Radiotherapy uses ionizing radiation to kill prostate cancer cells. When absorbed in tissue, Ionizing radiation such as Gamma and x-rays damage the DNA in cells, which increases the probability of apoptosis (cell death). Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) can be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy can have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It can also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Antiandrogens are medications such as flutamide, bicalutamide, nilutamide, and cyproterone acetate which directly block the actions of testosterone and DHT within prostate cancer cells. Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of LH directly, while GnRH agonists suppress LH through the process of down-regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

HIFU for prostate cancer utilizes high intensity focused ultrasound (HIFU) to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of affecting other tissue or organs. Temperatures at the focal point of the sound waves can exceed 100° C. HIFU procedure for prostate cancer is performed using a transrectal probe.

3. Gastric Cancer

Stomach cancer can develop in any part of the stomach and may spread throughout the stomach and to other organs; particularly the esophagus and the small intestine. Stomach cancer causes nearly one million deaths worldwide per year. To find the cause of symptoms, the doctor asks about the patient's medical history, does a physical exam, and may order laboratory studies. The patient may also have one or all of the following exams: gastroscopic exam, upper GI series (may be called barium roentgenogram), and fecal occult blood test. Abnormal tissue seen in a gastroscope examination can be biopsied by the surgeon or gastroenterologist. This tissue can then be sent to a pathologist for histological examination under a microscope to check for the presence of cancerous cells. A biopsy, with subsequent histological analysis can confirm the presence of cancer cells.

A condition of darkened hyperplasia of the skin, frequently of the axilla and groin, known as acanthosis nigricans, commonly prompts a study into gastric carcinoma. It should be noted that this hyperplasia can be found in obese individuals with no underlying cancer.

If cancer cells are found in the tissue sample, the next step is to stage, or find out the extent of the disease. Various tests determine whether the cancer has spread and, if so, what parts of the body are affected. Because stomach cancer can spread to the liver, the pancreas, and other organs near the stomach as well as to the lungs, the doctor may order a CT scan, a PET scan, an endoscopic ultrasound exam, or other tests to check these areas. Blood tests for tumor markers, such as carcinoembryonic antigen (CEA) and carbohydrate antigen (CA) can be ordered, as their levels correlate to extent of metastasis, especially to the liver, and the cure rate.

Like any cancer, treatment is adapted to fit each person's individual needs and depends on the size, location, and extent of the tumor, the stage of the disease, and general health. Cancer of the stomach is difficult to cure unless it is found in an early stage (before it has begun to spread). Unfortunately, because early stomach cancer causes few symptoms, the disease is usually advanced when the diagnosis is made. Treatment for stomach cancer may include surgery, chemotherapy, and/or radiation therapy. New treatment approaches such as biological therapy and improved ways of using current methods are being studied in clinical trials.

Surgery is the most common treatment for stomach cancer. The surgeon removes part or all of the stomach, as well as some of the tissue around the stomach, with the basic goal of removing all cancer and a margin of normal tissue. Depending on the extent of invasion and the location of the tumor, surgery may also include removal of part of the intestine or pancreas. Tumors in the lower parts of the stomach can call for a Billroth I or Billroth II procedure. Endoscopic mucosal resection is a treatment for early gastric cancer that has been pioneered in Japan, but is available in the United States at some centers. In this procedure, the tumor is removed from the wall of the stomach using an endoscope, with the advantage in that it is a smaller operation than removing the stomach. Surgical interventions are currently curative in less than 40% of cases, and, in cases of metastasis, may only be palliative.

Some chemotherapy drugs used in stomach cancer treatment include: 5-FU (fluorouracil), BCNU (carmustine), methyl-CCNU (Semustine), and doxorubicin (Adriamycin), as well as Mitomycin C, and more recently cisplatin and taxotere in various combinations. Chemotherapy can be given before surgery to shrink the tumor, or as adjuvant therapy after surgery to destroy remaining cancer cells. Also available are combination treatments with chemotherapy and radiation therapy. The anticancer drugs can be put directly into the abdomen (intraperitoneal hyperthermic chemoperfusion).

Radiation therapy can be used in combination with surgery and chemotherapy, or used only with chemotherapy in cases where the individual is unable to undergo surgery. Radiation therapy can also be used to relieve pain or blockage by shrinking the tumor for palliation of incurable disease 4. Lung Cancer The vast majority of primary lung cancers are carcinomas of the lung, derived from epithelial cells. Lung cancer, the most common cause of cancer-related death in men and the second most common in women, is responsible for 1.3 million deaths worldwide annually. The most common symptoms are shortness of breath, coughing (including coughing up blood), and weight loss.

The main types of lung cancer are small cell lung carcinoma and non-small cell lung carcinoma. This distinction is important because the treatment varies; non-small cell lung carcinoma (NSCLC) is sometimes treated with surgery, while small cell lung carcinoma (SCLC) usually responds better to chemotherapy and radiation. The most common cause of lung cancer is long term exposure to tobacco smoke. The occurrence of lung cancer in non-smokers, who account for fewer than 10% of cases, appears to be due to a combination of genetic factors, radon gas, asbestos, and air pollution, including second-hand smoke.

Lung cancer can be seen on chest x-ray and computed tomography (CT scan). The diagnosis is confirmed with a biopsy. This is usually performed via bronchoscopy or CT-guided biopsy. Treatment and prognosis depend upon the histological type of cancer, the stage (degree of spread), and the patient's performance status. Possible treatments include surgery, chemotherapy, and radiotherapy. With treatment, the five-year survival rate is 14%.

The vast majority of lung cancers are carcinomas—malignancies that arise from epithelial cells. There are two main types of lung carcinoma, categorized by the size and appearance of the malignant cells seen by a histopathologist under a microscope: non-small cell (80.4%) and small-cell (16.8%) lung carcinoma. This classification, based on histological criteria, has important implications for clinical management and prognosis of the disease.

The non-small cell lung carcinomas are grouped together because their prognosis and management are similar. There are three main sub-types: squamous cell lung carcinoma, adenocarcinoma and large cell lung carcinoma. Accounting for 31.1% of lung cancers, squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 29.4% of lung cancers. It usually originates in peripheral lung tissue. Most cases of adenocarcinoma are associated with smoking. However, among people who have never smoked ("never-smokers"), adenocarcinoma is the most common form of lung cancer. A subtype of adenocarcinoma, the bronchioloalveolar carcinoma, is more common in female never-smokers, and may have different responses to treatment. Accounting for 10.7% of lung cancers, large cell lung carcinoma is a fast-growing form that develops near the surface of the lung. It is often poorly differentiated and tends to metastasize early.

Small cell lung carcinoma (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones) which give this an endocrine/paraneoplastic syndrome association. While initially more sensitive to chemotherapy, it ultimately carries a worse prognosis and is often metastatic at presentation. Small cell lung cancers are divided into Limited stage and Extensive stage disease. This type of lung cancer is strongly associated with smoking.

The lung is a common place for metastasis from tumors in other parts of the body. These cancers are identified by the site of origin, thus a breast cancer metastasis to the lung is still known as breast cancer. They often have a characteristic round appearance on chest x-ray. Primary lung cancers themselves most commonly metastasize to the adrenal glands, liver, brain, and bone.

Lung cancer staging is an assessment of the degree of spread of the cancer from its original source. It is an important factor affecting the prognosis and potential treatment of lung cancer. Non-small cell lung carcinoma is staged from IA ("one A", best prognosis) to IV ("four", worst prognosis). Small cell lung carcinoma is classified as limited stage if it is confined to one half of the chest and within the scope of a single radiotherapy field. Otherwise it is extensive stage.

Performing a chest x-ray is the first step if a patient reports symptoms that may be suggestive of lung cancer. This can reveal an obvious mass, widening of the mediastinum (suggestive of spread to lymph nodes there), atelectasis (collapse), consolidation (pneumonia), or pleural effusion. If there are no x-ray findings but the suspicion is high (such as a heavy smoker with blood-stained sputum), bronchoscopy and/or a CT scan can provide the necessary information. Bronchoscopy or CT-guided biopsy is often used to identify the tumor type. Treatment for lung cancer depends on the cancer's specific cell type, how far it has spread, and the patient's performance status. Common treatments include surgery, chemotherapy, and radiation therapy. If investigations confirm lung cancer, CT scan and often positron emission tomography (PET) can be used to determine whether the disease is localised and amenable to surgery or whether it has spread to the point where it cannot be cured surgically. Blood tests and spirometry (lung function testing) can be used to assess whether the patient is well enough to be operated on. If spirometry reveals poor respiratory reserve (often due to chronic obstructive pulmonary disease), surgery may be contraindicated.

Surgery itself has an operative death rate of about 4.4%, depending on the patient's lung function and other risk factors. Surgery is usually only an option in non-small cell lung carcinoma limited to one lung, up to stage IIIA. This can be assessed with medical imaging (computed tomography, positron emission tomography). A sufficient pre-operative respiratory reserve must be present to allow adequate lung function after the tissue is removed.

Procedures include wedge resection (removal of part of a lobe), segmentectomy (removal of an anatomic division of a particular lobe of the lung), lobectomy (one lobe), bilobectomy (two lobes) or pneumonectomy (whole lung). In patients with adequate respiratory reserve, lobectomy is generally the preferred option, as this minimizes the chance of local recurrence. If the patient does not have enough functional lung for this, wedge resection can be performed. Radioactive iodine brachytherapy at the margins of wedge excision can reduce recurrence to that of lobectomy.

Small cell lung carcinoma can be treated primarily with chemotherapy and radiation. Primary chemotherapy can also be given in metastatic non-small cell lung carcinoma.

The combination regimen depends on the tumor type. Non-small cell lung carcinoma can be treated with cisplatin or carboplatin, in combination with gemcitabine, paclitaxel, docetaxel, etoposide or vinorelbine. In small cell lung carcinoma, cisplatin and etoposide can be used. Combinations with carboplatin, gemcitabine, paclitaxel, vinorelbine, topotecan and irinotecan can also be used.

Adjuvant chemotherapy refers to the use of chemotherapy after surgery to improve the outcome. During surgery, samples are taken from the lymph nodes. If these samples contain cancer, then the patient has stage II or III disease. In this situation, adjuvant chemotherapy can improve survival by up to 15%. For example, the patient can be treated with platinum-based chemotherapy (including either cisplatin or carboplatin).

Radiotherapy is often given together with chemotherapy, and can be used with curative intent in patients with non-small cell lung carcinoma who are not eligible for surgery. This form of high intensity radiotherapy is called radical radiotherapy. A refinement of this technique is continuous hyperfractionated accelerated radiotherapy (CHART), where a high dose of radiotherapy is given in a short time period. For small cell lung carcinoma cases that are potentially curable, in addition to chemotherapy, chest radiation is often recommended.

For both non-small cell lung carcinoma and small cell lung carcinoma patients, smaller doses of radiation to the chest may be used for symptom control (palliative radiotherapy). Unlike other treatments, it is possible to deliver palliative radiotherapy without confirming the histological diagnosis of lung cancer.

Patients with limited stage small cell lung carcinoma are usually given prophylactic cranial irradiation (PCI). This is a type of radiotherapy to the brain, used to reduce the risk of metastasis. More recently, PCI has also been shown to be beneficial in those with extensive small cell lung cancer. In patients whose cancer has improved following a course of chemotherapy, PCI has been shown to reduce the cumulative risk of brain metastases within one year from 40.4% to 14.6%.

Extracranial stereotactic radiation can be used in the treatment of early-stage lung cancer. In this form of radiation therapy, very high doses are delivered in a small number of sessions using stereotactic targeting techniques. Its use is primarily in patients who are not surgical candidates due to medical comorbidities.

Radiofrequency ablation can be used in the treatment of bronchogenic carcinoma. It is done by inserting a small heat probe into the tumor to kill the tumor cells.

Various molecular targeted therapies have been developed for the treatment of advanced lung cancer. Gefitinib (Iressa) is one such drug, which targets the tyrosine kinase domain of the epidermal growth factor receptor (EGF-R) which is expressed in many cases of non-small cell lung carcinoma. Erlotinib (Tarceva), another tyrosine kinase inhibitor, has been shown to increase survival in lung cancer patients and has recently been approved by the FDA for second-line treatment of advanced non-small cell lung carcinoma. The angiogenesis inhibitor bevacizumab (in combination with paclitaxel and carboplatin) can be used to improve the survival of patients with advanced non-small cell lung carcinoma.

Other treatments include cyclo-oxygenase-2 inhibitors, the apoptosis promoter exisulind, proteasome inhibitors, bexarotene, vaccines, ras proto-oncogene inhibition, phosphoinositide 3-kinase inhibition, histone deacetylase inhibition, and tumor suppressor gene replacement.

B. Methods and Compositions

Bcl-B can be detected using any suitable method, technique and compositions. Many general assays and assay compositions are known and can be used or adapted to detect Bcl-B. Certain methods and compositions may be better suited to detecting Bcl-B expression, Bcl-B expression levels, or cells expressing Bcl-B. Those of skill in the art are aware of how to apply known techniques for these purposes. Some useful methods, techniques and compositions are discussed below.

1. Immunohistochemistry

Disclosed herein are immunohistochemistry methods that can be used to detect Bcl-B in cancer cells for use in the methods disclosed herein. In some aspects, the method comprises immunolabeling Bcl-B in cancer tissue and creating a digital image of the immunolabeling. In some aspects, the digital image is analyzed to count the percentage of immunolabled cells. Other such adaptations of standard immunohistochemistry methods are known and can be used in the disclosed methods.

Immunohistochemistry or IHC refers to the process of localizing proteins in cells of a tissue section exploiting the principle of antibodies binding specifically to antigens in biological tissues. It takes its name from the roots "immuno," in reference to antibodies used in the procedure, and "histo," meaning tissue (compare to immunocytochemistry). Immunohistochemical staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue.

Visualising an antibody-antigen interaction can be accomplished in a number of ways. In the most common instance, an antibody is conjugated to an enzyme, such as peroxidase, that can catalyse a colour-producing reaction (see immunoperoxidase staining). Alternatively, the antibody can also be tagged to a fluorophore, such as FITC, rhodamine, Texas Red, Alexa Fluor, or DyLight Fluor (see immunofluorescence). The latter method is of great use in confocal laser scanning microscopy, which is highly sensitive and can also be used to visualise interactions between multiple proteins.

There are two strategies used for the immunohistochemical detection of antigens in tissue, the direct method and the indirect method. In both cases, the tissue is treated to rupture the membranes, usually by using a kind of detergent such as Triton X-100. Some antigen also need additional step for unmasking, resulting in better detection results.

The direct method is a one-step staining method, and involves a labeled antibody (e.g. FITC conjugated antiserum) reacting directly with the antigen in tissue sections. This technique utilizes only one antibody and the procedure is therefore simple and rapid. However, it can suffer problems with sensitivity due to little signal amplification and is in less common use than indirect methods.

The indirect method involves an unlabeled primary antibody (first layer) which reacts with tissue antigen, and a labeled secondary antibody (second layer) which reacts with the primary antibody. (The secondary antibody must be against the IgG of the animal species in which the primary antibody has been raised.) This method is more sensitive due to signal amplification through several secondary antibody reactions with different antigenic sites on the primary antibody. The second layer antibody can be labeled with a fluorescent dye or an enzyme.

2. Immunoassay

Disclosed herein are immunoassays that can be used to detect Bcl-B in cancer cells for use in the methods disclosed herein. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminance. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO— TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson—; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP);

SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Reds; Texas Red-X™ conjugate; Thiadicarbocyanine (DiSC3); Thiazine Red™; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-genrating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

An immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452, 901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

Also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995;U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDOts™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a polylysine backbone immobilised on a surface such as titanium dioxide (Zyomyx) or tantalum pentoxide (Zeptosens, Witterswil, Switzerland).

Array fabrication methods include robotic contact printing, inkjetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

3. Separation Methods

Disclosed herein are separation methods that can be used to detect the number or percentage of cells with detectable Bcl-B expression for use in the methods disclosed herein. Cells with detectable Bcl-B expression can be isolated by a fluorescence activated cell sorting (FACS), protein-conjugated magnetic bead separation, specific gene expression patterns (using RT-PCR), or specific antibody staining.

Cells may be selected based on light-scatter properties as well as their expression of various cell surface antigens. Various techniques can be employed to separate the cells with detectable Bcl-B expression. Monoclonal antibodies are particularly useful. The antibodies can be attached to a solid support to allow for crude separation. The separation techniques employed should maximize the retention of viability of the fraction to be collected.

Procedures for separation can include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

The antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

4. Antibodies

Disclosed herein are antibodies that specifically bind Bcl-B that can be used to detect Bcl-B in cancer cells. For example, disclosed is a polyclonal antibody specific for Bcl-B raised in a mammal using Bcl-B protein, or an immunogenic fragment thereof as the immunogen. For example, disclosed is a polyclonal antibody specific for Bcl-B (BR-49) that was raised in rabbits using the affinity purified recombinant GST-Bcl-B protein as the immunogen. Also disclosed is anti-Bcl-B serum (AR-77) generated in rabbits using a synthetic peptide ($NH_2$—REPGTPEPAPSTPEAAVLR-amide; SEQ ID NO: 1) corresponding to residues 32 to 50 of human Bcl-B.

Thus, the immunogenic fragment of Bcl-B can comprise residues 32, 33, 34, 35, 36, 37, 38, 39, 40, 41, 42, 43, 44, 45, 46 to 50 of human Bcl-B. Thus, the immunogenic fragment of Bcl-B can comprise residues 32, 33, 34, 35, 36, 37, 38, 39, 40, 41, 42, 43, 44, 45 to 49 of human Bcl-B. Thus, the immunogenic fragment of Bcl-B can comprise residues 32, 33, 34, 35, 36, 37, 38, 39, 40, 41, 42, 43, 44 to 48 of human Bcl-B. Thus, the immunogenic fragment of Bcl-B can comprise residues 32, 33, 34, 35, 36, 37, 38, 39, 40, 41, 42, 43 to 47 of human Bcl-B. Thus, the immunogenic fragment of Bcl-B can comprise residues 32, 33, 34, 35, 36, 37, 38, 39, 40, 41, 42 to 46 of human Bcl-B. Thus, the immunogenic fragment of Bcl-B can comprise residues 32, 33, 34, 35, 36, 37, 38, 39, 40, 41 to 45 of human Bcl-B. Thus, the immunogenic fragment of Bcl-B can comprise residues 32, 33, 34, 35, 36, 37, 38, 39, 40 to 44 of human Bcl-B. Thus, the immunogenic fragment of Bcl-B can comprise residues 32, 33, 34, 35, 36, 37, 38, 39 to 43 of human Bcl-B. Thus, the immunogenic fragment of Bcl-B can comprise residues 32, 33, 34, 35, 36, 37, 38 to 42 of human Bcl-B. Thus, the immunogenic fragment of Bcl-B can comprise residues 32, 33, 34, 35, 36, 37 to 41 of human Bcl-B. Thus, the immunogenic fragment of Bcl-B can comprise residues 32, 33, 34, 35, 36 to 40 of human Bcl-B. Thus, the immunogenic fragment of Bcl-B can comprise residues 32, 33, 34, 35 to 39 of human Bcl-B. Thus, the immunogenic fragment of Bcl-B can comprise residues 32, 33, 34 to 38 of human Bcl-B. Thus, the immunogenic fragment of Bcl-B can comprise residues 32, 33 to 37 of human Bcl-B. Thus, the immunogenic fragment of Bcl-B can comprise residues 32 to 36 of human Bcl-B.

Thus, the immunogenic fragment of Bcl-B can comprise residues 32 to 36, 37, 38, 39, 40, 41, 42, 43, 44, 45, 46, 47, 48, 49, or 50 of human Bcl-B. Thus, the immunogenic fragment of Bcl-B can comprise residues 33 to 37, 38, 39, 40, 41, 42, 43, 44, 45, 46, 47, 48, 49, or 50 of human Bcl-B. Thus, the immunogenic fragment of Bcl-B can comprise residues 34 to 38, 39, 40, 41, 42, 43, 44, 45, 46, 47, 48, 49, or 50 of human Bcl-B. Thus, the immunogenic fragment of Bcl-B can comprise residues 35 to 39, 40, 41, 42, 43, 44, 45, 46, 47, 48, 49, or 50 of human Bcl-B. Thus, the immunogenic fragment of Bcl-B can comprise residues 36 to 40, 41, 42, 43, 44, 45, 46, 47, 48, 49, or 50 of human Bcl-B. Thus, the immunogenic fragment of Bcl-B can comprise residues 37 to 41, 42, 43, 44, 45, 46, 47, 48, 49, or 50 of human Bcl-B. Thus, the immunogenic fragment of Bcl-B can comprise residues 38 to 42, 43, 44, 45, 46, 47, 48, 49, or 50 of human Bcl-B. Thus, the immunogenic fragment of Bcl-B can comprise residues 39 to 43, 44, 45, 46, 47, 48, 49, or 50 of human Bcl-B. Thus, the immunogenic fragment of Bcl-B can comprise residues 40 to 44, 45, 46, 47, 48, 49, or 50 of human Bcl-B. Thus, the immunogenic fragment of Bcl-B can comprise residues 41 to 45, 46, 47, 48, 49, or 50 of human Bcl-B. Thus, the immunogenic fragment of Bcl-B can comprise residues 42 to 46, 47, 48, 49, or 50 of human Bcl-B. Thus, the immunogenic fragment of Bcl-B can comprise residues 43 to 47, 48, 49, or 50 of human Bcl-B. Thus, the immunogenic fragment of Bcl-B can comprise residues 44 to 48, 49, or 50 of human Bcl-B. Thus, the immunogenic fragment of Bcl-B can comprise residues 45 to 49, or 50 of human Bcl-B. Thus, the immunogenic fragment of Bcl-B can comprise residues 46 to 50 of human Bcl-B.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with Bcl-B. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

If these approaches do not produce neutralizing antibodies, cells expressing cell surface localized versions of these proteins will be used to immunize mice, rats or other species. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding extracellular fragments of Bcl-B expressed as a fusion protein with human IgG1 or an epitope tag is injected into the host animal according to methods known in the art (e.g., Kilpatrick K E, et al. Hybridoma. 1998 December; 17(6):569-76; Kilpatrick K E et al. Hybridoma. 2000 August; 19(4):297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing the immunogenic fragment of Bcl-B as fusion proteins with a signal sequence fragment. The antigen is produced by inserting a gene fragment in-frame between the signal sequence and the mature protein domain of Bcl-B nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against Bcl-B. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones can be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

The term "antibody" as used herein is meant to include intact molecules as well as fragments thereof, such as, for example, Fab and F(ab')$_2$, which are capable of binding the epitopic determinant.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain Bcl-B binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with Bcl-B. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

Techniques can also be adapted for the production of single-chain antibodies specific to an antigenic protein of the present disclosure (see e.g., U.S. Pat. No. 4,946,778). In addition, methods can be adapted for the construction of F (ab) expression libraries (see e.g., Huse, et al., 1989 Science 246: 1275-1281) to allow rapid and effective identification of monoclonal F (ab) fragments with the desired specificity for a protein or derivatives, fragments, analogs or homologs thereof. Antibody fragments that contain the idiotypes to a protein antigen may be produced by techniques known in the art including, but not limited to: (i) an F ((ab'))(2) fragment produced by pepsin digestion of an antibody molecule; (ii) an Fab fragment generated by reducing the disulfide bridges of an F ((ab'))(2) fragment; (iii) an F (ab) fragment generated by the treatment of the antibody molecule with papain and a reducing agent and (iv) F (v), fragments.

Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding (Bedzyk et al., 1990; Chaudhary et al., 1990). The linker is chosen to permit the heavy chain and light chain to bind together in their proper conformational orientation. See, for example, Huston, J. S., et al., Methods in Enzym. 203:46-121 (1991), which is incorporated herein by reference. These Fvs lack the constant regions (Fc) present in the heavy and light chains of the native antibody.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. As used herein, the term "hybrid antibody" refers to an antibody wherein each chain is separately homologous with reference to a mammalian antibody chain, but the combination represents a novel assembly so that two different antigens are recognized by the antibody. Such hybrids can be formed by fusion of hybridomas producing the respective component antibodies, or by recombinant techniques. Such hybrids may, of course, also be formed using chimeric chains.

The encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

The antibody can be bound to a substrate or labeled with a detectable moiety or both bound and labeled. The detectable moieties contemplated with the present compositions include fluorescent, enzymatic and radioactive markers.

5. Nucleic Acid Detection

Disclosed herein are methods for detecting and determining the abundance of Bcl-B nucleic acid, such as mRNA, in a total or poly(A) RNA sample from cancer cells for use in the methods disclosed herein. For example, specific mRNAs can be detected using Northern blot analysis, nuclease protection assays (NPA), in situ hybridization, or reverse transcription-polymerase chain reaction (RT-PCR).

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

Northern analysis presents several advantages over the other techniques. The most compelling of these is that it is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 μg of sample RNA, compared with the 20-30 μg maximum of blot hybridizations. NPAs are also less sensitive to RNA sample degradation than Northern analysis since cleavage is only detected in the region of overlap with the probe (probes are usually about 100-400 bases in length).

NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

RT-PCR has revolutionized the study of gene expression. It is now theoretically possible to detect the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR. As with NPAs, RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) can vary in expression. Additionally, most common internal controls are expressed at much higher levels than the mRNA being studied. Preferably, all products of the PCR reaction can be analyzed in the linear range of amplification, which becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

6. Primers and Probers

Disclosed herein are nucleic acids that can be used to detect Bcl-B in cancer cells for use in the methods disclosed herein. For example, disclosed are compositions including primers and probes, which are capable of interacting with Bcl-B transcript.

The nucleic acid sequence for human Bcl-B is set forth in Accession No. AF285092 (SEQ ID NO:2), and the amino acid sequence is set forth in Accession No. AAG00503 (SEQ ID NO:3).

In certain embodiments the primers are used to support DNA (e.g., cDNA) amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the Bcl-B gene or transcript typically will be used to produce an amplified DNA product that contains a region of the Bcl-B gene or transcript or the complete gene or transcript. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The disclosed nucleic acids can be made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

C. DEFINITIONS

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

As used herein, the term "epitope" is meant to include any determinant capable of specific interaction with the anti-Bcl-B antibodies disclosed. Epitopic determinants usually consist of chemically active surface groupings of molecules such as amino acids or sugar side chains and usually have specific three dimensional structural characteristics, as well as specific charge characteristics.

An "epitope tag" denotes a short peptide sequence unrelated to the function of the antibody or molecule that can be used for purification or crosslinking of the molecule with anti-epitope tag antibodies or other reagents.

By "specifically binds" is meant that an antibody recognizes and physically interacts with its cognate antigen and does not significantly recognize and interact with other antigens; such an antibody may be a polyclonal antibody or a monoclonal antibody, which are generated by techniques that are well known in the art.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Bcl-B Expression in Human Epithelial and Non-epithelial Malignancies i. Materials and Methods
a. Patient Specimens Bone marrow biopsies from 165 patients, 114 with symptomatic multiple myeloma (MM), 19 with indolent MM, 13 with monoclonal gammopathy of undetermined significance (MGUS), and 19 with reactive plasmacytosis, were obtained from VA Hospital of Los Angeles. Patients were categorized according to WHO criteria, assessing the plasma count in bone marrow (group 1: 0-10%, group 2: 11-30%, group 3: >30%)(Went P, et al. 2006).

Tissue microarrays (TMAs) comprising paraffin-embedded lymph node specimens from 48 patients diagnosed with DLBCL and from 57 patients with FL were obtained. Tumor specimens were obtained from 79 SCLC patients with limited disease who were treated by surgery followed by chemotherapy using various multidrug regimens between 1984 and 2001. In addition, thoracic radiation was administered to 4% and prophylactic cranial irradiation to 8% of the patients. Patients ranged from clinical stage I-IIIA and were of good performance status (Karnofsky score 80-100). Clinical data represent a median follow up of 1.3 years. TMAs containing specimens from 82 NSCLC patients were obtained. The specimens represented 22 adenocarcinomas, 32 squamous cell carcinomas, and 16 large cell carcinomas (12 unspecified tumors).

Clinicopathological characteristics related to paraffin-embedded tissue specimens containing cervical, colorectal, gastric, breast, prostate and ovarian cancers were described (Krajewska M, et al. 2005a; Krajewska M, et al. 2005b; Krajewska M, et al. 2007; Meinhold-Heerlein I, et al. 2001). In addition, a TMA was produced for 26 cases of Crohn's disease.

b. Tissue Preparation

The tissues were prepared for paraffin embedding, as described (Krajewska M, et al. 2003). TMAs were produced for all investigated tumors and tissues, as described previously (Krajewska M, et al. 2005b).

c. Antibodies

Glutatione S-transferase (GST)-Bcl-B fusion protein was produced in bacteria and purified by affinity chromatography as described (Zhai D, et al. 2006). A polyclonal antibody specific for Bcl-B (BR-49) was raised in rabbits using the affinity purified recombinant GST-Bcl-B protein as the immunogen. An additional anti-Bcl-B serum (AR-77) was generated in rabbits using a synthetic peptide ($NH_2$-REPGT- PEPAPSTPEAAVLR-amide; SEQ ID NO: 1) corresponding to residues 32 to 50 of human Bcl-B. Commercial mouse monoclonal antibodies included anti-CD138 (Serotec, Raleigh, N.C.), anti-CD68 (DakoCytomation, Carpinteria, Calif.), anti-CD10 (Novocastra, Newcastle Upon Tyne, England), anti-Bcl-6 (Novocastra), anti-MUM1 (DakoCytomation), anti-Bcl-2 (DakoCytomation), anti-Hsp60 (Nventa, Victoria, BC, Canada), anti-β-actin (Sigma-Aldrich, St Louis, Mo.), and anti-GST (BD Pharmingen, San Diego, Calif.)

d. Immunohistochemistry (IHC)

Dewaxed tissue sections were immunostained as reported (Krajewski S, et al. 1999). To determine specificity, the immunostaining procedure was performed in parallel using preimmune Bcl-B serum and immune serum (1:1000) preabsorbed with 10 μg of GST-Bcl-B, GST-Bcl-$X_L$ recombinant protein or synthetic peptide immunogens. The immunostaining scoring system was described (Krajewska M, et al. 2002).

For double-labeling procedure, tissue sections were stained as above using Bcl-B rabbit polyclonal antiserum (DAB chromagen, DAKOCytomation) followed by mouse monoclonal CD138 antibody (Serotec)(SG chromagen, Vector Lab. Inc). Nuclear Red (DAKOCytomation) was used for counterstaining of the double-labeled slides. Automated image analysis system (Aperio Technology Inc, Vista Calif.) was employed to visualize Bcl-B and CD 138 staining separately, applying a color deconvolution algorithm (Ruifrok A C, et al. 2001). Quantification of immunostaining was performed using color translation and an automated thresholding algorithm (Aperio Technology Inc).

IHC results for CD10, Bcl-6, and MUM1 were used to subclassify DLBCL cases into GCB and non-GCB categories (Hans C P, et al. 2004): cases immunopositive for CD10 alone or for both CD10 and Bcl-6 were assigned to the GCB group, while cases that were CD10$^-$/Bcl-6$^-$ or that were CD10$^-$/Bcl-6$^+$/MUM1$^+$ were considered non-GCB.

e. Expression Plasmids

Bcl-B encoding cDNA in pcDNA3-Bcl-B plasmid was digested with BamHI and XhoI (Promega, USA), purified (Qiagen) from a 1% agarose gel, and then ligated with modified pTRE2hyg plasmid (Clontech, USA) previously digested with the same restriction enzymes. Proper plasmid construction was confirmed by restriction-enzyme digestion and DNA sequencing.

f. Stable Transfection

Stable transfection was conducted using the HeLa Tet-on cell line (Clontech, USA), which was derived from the HeLa cells. This cell line had been stably transfected with the pTet-On plasmid, which encoded the tetracycline repressor and allowed the inserted sequence to be inducibly expressed by tetracycline or doxycycline. The HeLa Tet-on cells were seeded at 50% confluency and cultured overnight. Transfection was conducted for 3 hours using LipofectAMINE PLUS. Transfected cells were cultured in complete media for 24 hours and then split into fresh media. The split cells were seeded to 10% confluence and cultured in media containing G418 (100 μg/ml) to maintain the integrity of the pTet-On construct and hygromycin B (300 μg/ml) to select stable transfectants of pTRE2hyg/Bcl-B. Positive foci resistant to both antibiotics were isolated and expanded. The transfected cells were cultured in the presence or absence of doxycycline (1 μg/ml) for 16 hours for immunoblot studies.

g. Immunoblotting

Specimens derived from normal and malignant human tissues with high ratios of cancer cells relative to stroma (>70%) were provided by M. D. Anderson Cancer Center Orlando for immunoblotting analysis. The protein lysate preparations, immunoblotting procedures, and antigen detection were described previously (Krajewski S, et al. 1996). Blots were probed with rabbit anti-Bcl-2 antisera (1:2000-1:3000 v/v), mouse anti-Hsp60 or β-actin antibodies. Expression and purification of recombinant Bcl-2-family proteins are described elsewhere (Luciano F, et al. 2007).

h. Microsatellite Instability (MSI)

Specimens were analyzed for MSI as described (Krajewska M, et al. 2005b).

i. Statistical Analysis

Figure 1B:
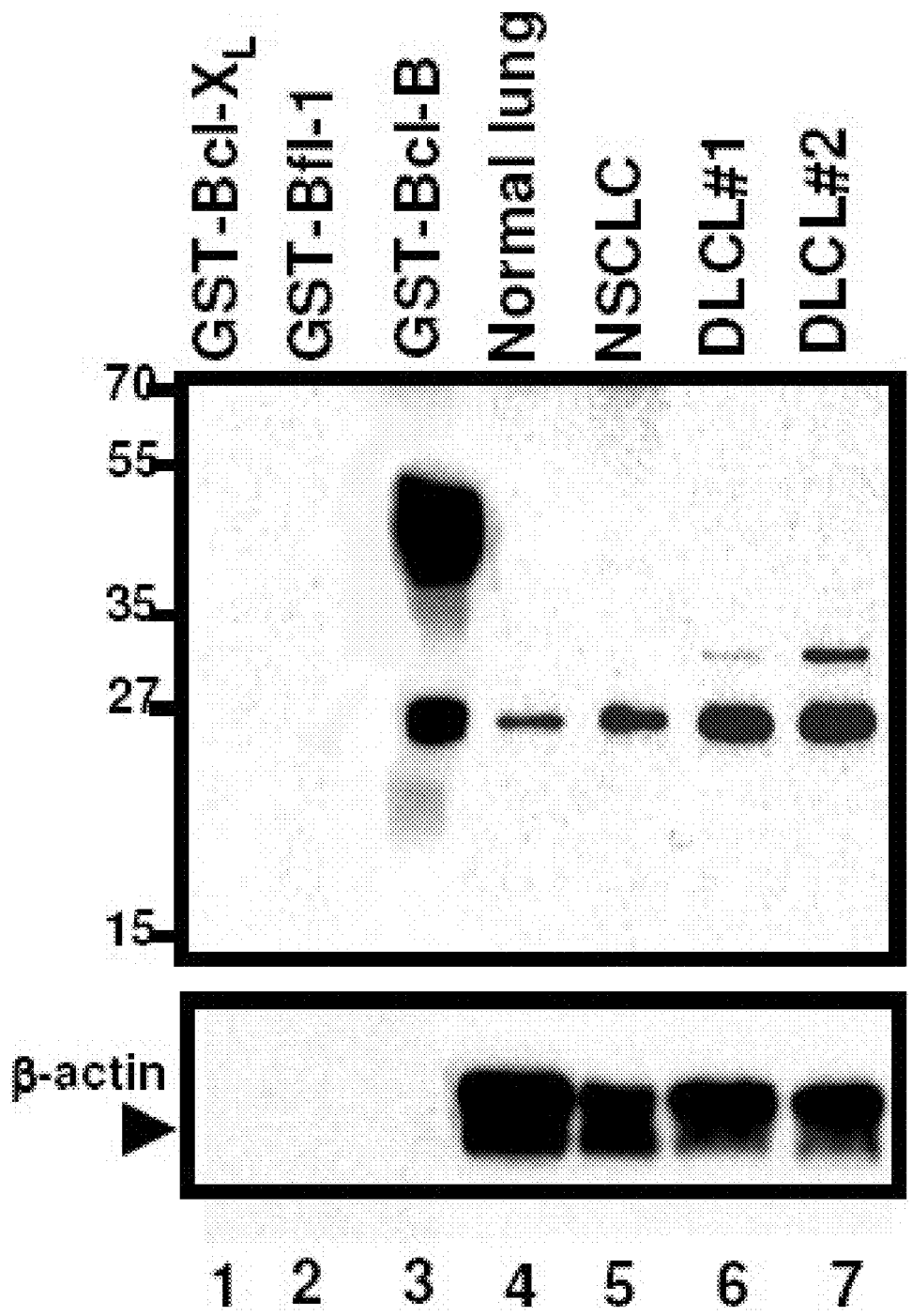

Data were analyzed using the STATISTICA software package (StatSoft) as described elsewhere (Krajewska M, et al. 2005b). Median Bcl-B immunopercentage and immunoscore were applied as cut-offs for Kaplan-Meier survival analyses.

ii. Results a. Characterization of Bcl-B Antibodies and Immunoblot Analysis of Normal and Malignant Human Tissues The specificity of the BR-49 antibody was documented, showing reactivity with Bcl-B but not Bcl-2, Bcl-$X_L$, Mcl-1, Bcl-W or Bfl-1 (Luciano F, et al. 2007). To characterize the specificity of the AR-77 antibody, immunoblot analysis was performed using recombinant Bcl-2 family proteins generated in bacteria (FIG. 1A-B). The AR-77 antibody was determined to be specific for Bcl-B, detecting GST fusion protein containing Bcl-B and lacking cross-reactivity with other Bcl-2-family members (FIG. 1A-B). Note that the two bands seen with GST-Bcl-B likely correspond to intact fusion protein (~45-50 kD) and proteolyzed protein separating Bcl-B (~23 kD) from GST.

Probing tissue lysates with the AR-77 or BR-49 antibodies showed reactivity with a protein at ~23 kD, corresponding to the predicted molecular mass of Bcl-B, as well as ~45-50 kD band that appears to be an SDS-resistant dimer, based on studies that have detected this species even when using epitope-tagged Bcl-B protein that was detected using antibodies directed against the tag. Also, a dimeric form of Bcl-B was demonstrated by SDS-PAGE analyses of purified recombinant Bcl-B produced without GST tag. In some tumor lysates, bands were detected that may correspond to post-translationally modified forms of Bcl-B, which migrate at a few kilo-Daltons larger apparent molecular mass than monomeric Bcl-B in SDS-PAGE (see for example DLCL, MM and BPH samples). The specificity of the anti-Bcl-B antibodies was further confirmed by analysis of lysates from HeLa cells containing a tetracycline-inducible Bcl-B construct, revealing the presence of the expected ~23 kD Bcl-B band only when the tetracycline analog doxycyclin was added to cultures (FIG. 1).

Figure 1C:
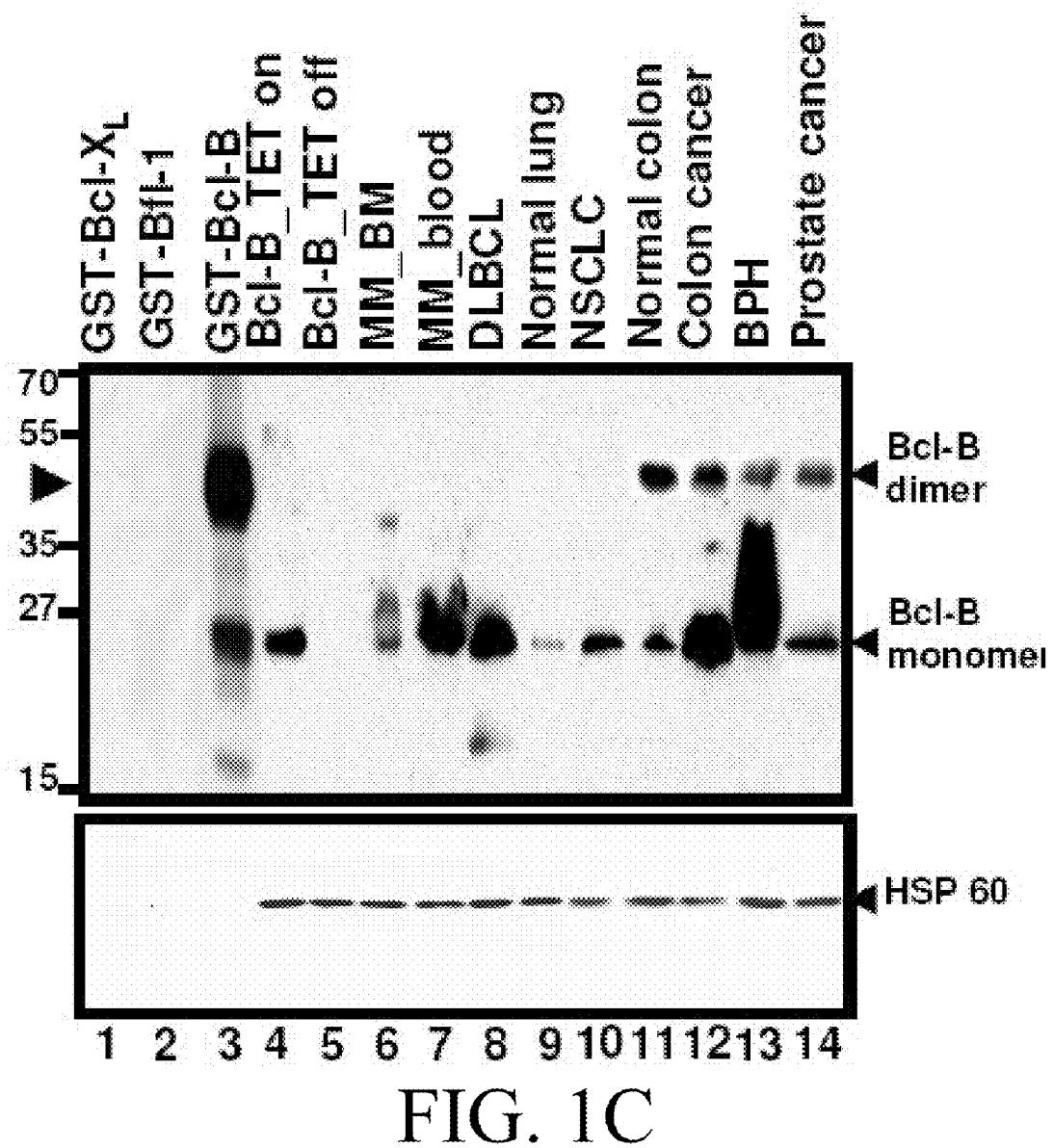
Figure 2:
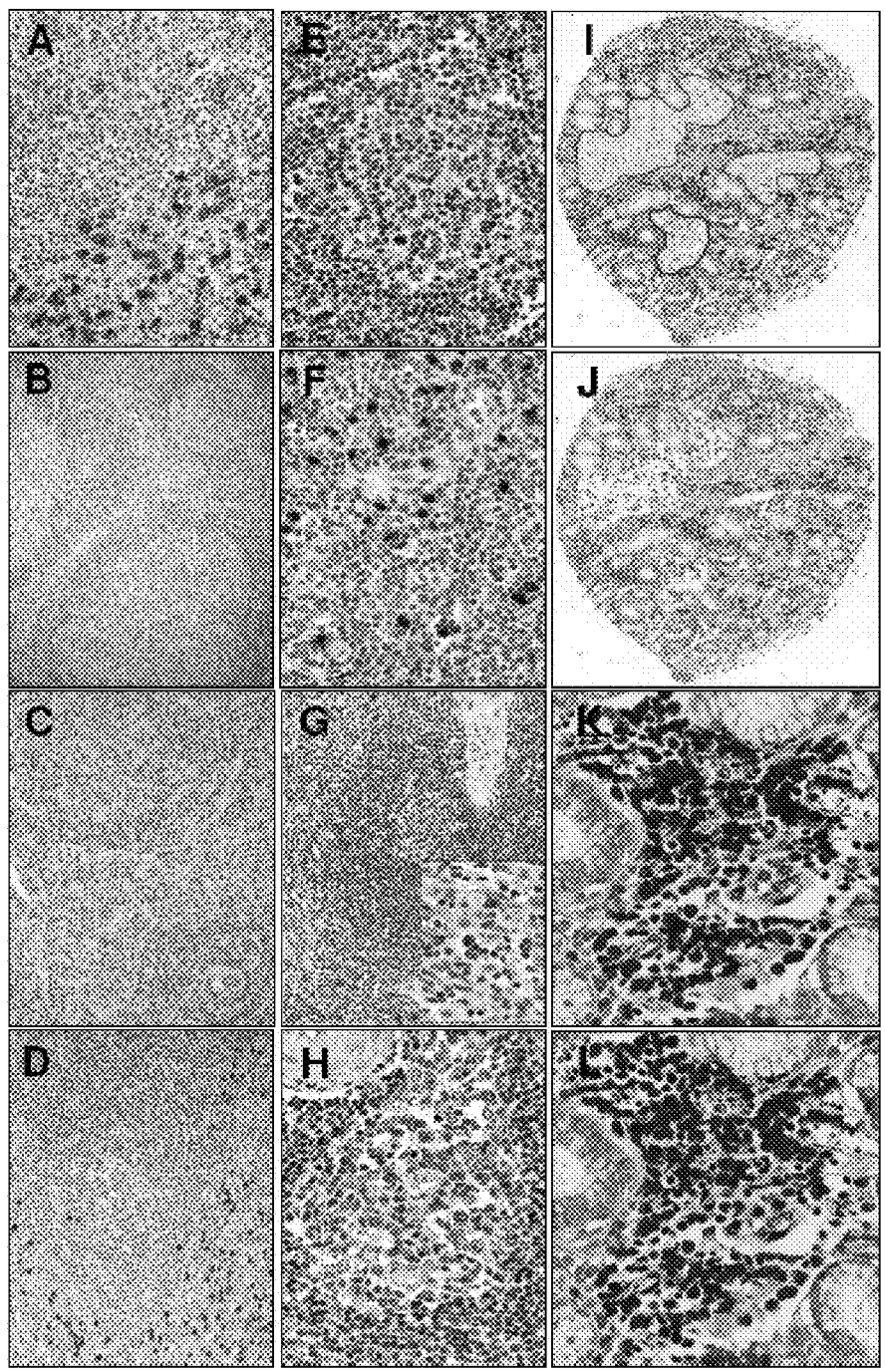
FIGS. 2A-2L show immunohistochemical detection of Bcl-B expression in B cells and plasma cells.
Figure 6A:
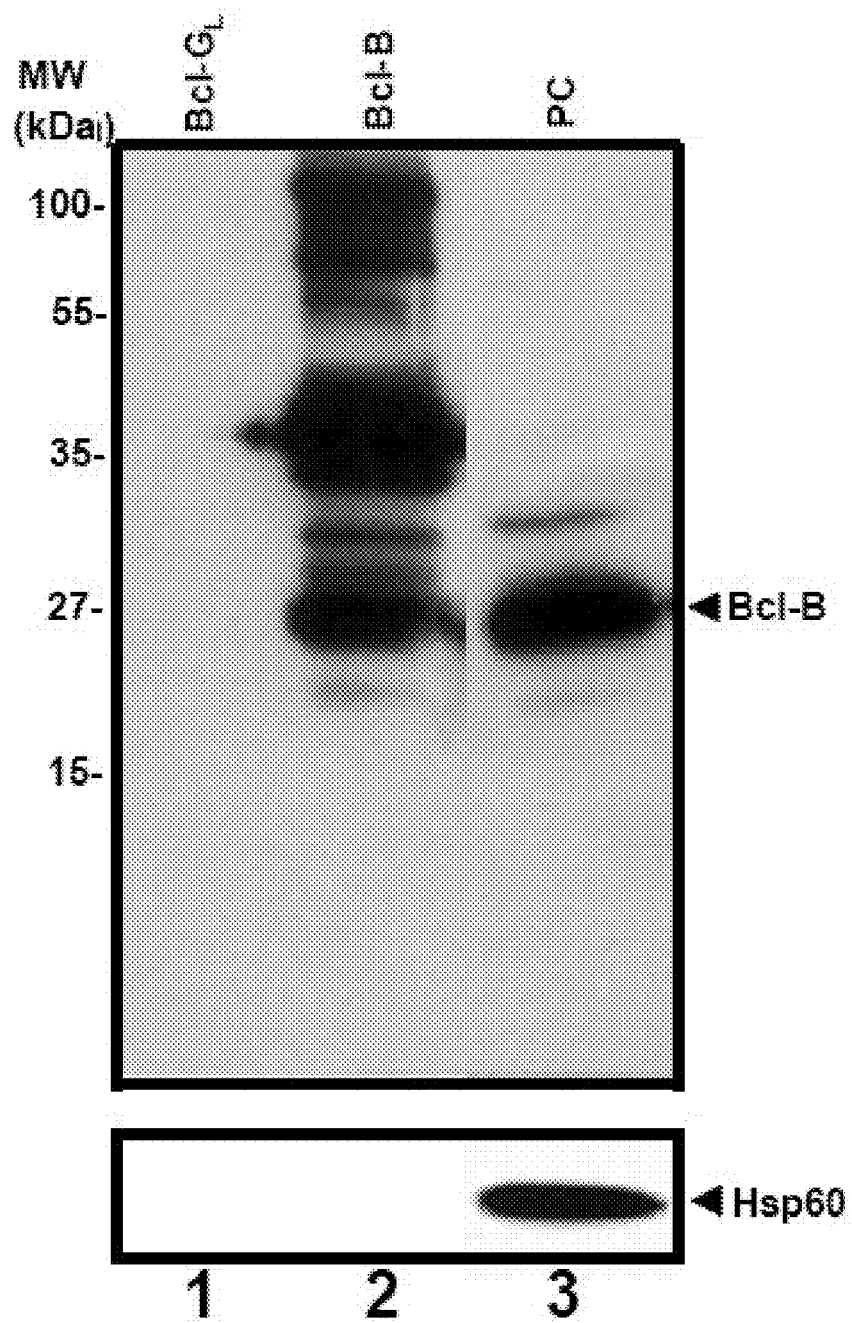
FIGS. 6A, 6B, and 6C show immunoblot analysis of plasma Cells confirms Bcl-B expression. Plasma cells (PC) were isolated from a human normal bone marrow suspension using CD 138+ human plasma cell isolation kit from Miltenyi Biotec according to the manufacturer's instruction. Briefly, CD138-expressing cells were separated by magnetic labeling with CD 138 microbeads and enrichment of labeled cells using magnetic cell sorting (MACS). Giemsa staining showed enrichment at 86.1±7.3% from 3 experiments. In addition, plasma cell fractions were isolated from bone marrow aspirates derived from 4 patients with multiple myeloma. Cell lysates were analyzed by immunoblotting as described in the manuscript, probing blots with rabbit anti-Bcl-B antibodies (whole serum or affinity purified) [top] or with mouse monoclonal antibodies directed against Hsp60 or β3-actin [bottom]. Molecular weight (MW) markers are shown in kilo-Daltons (kDa).
Figure 6B:
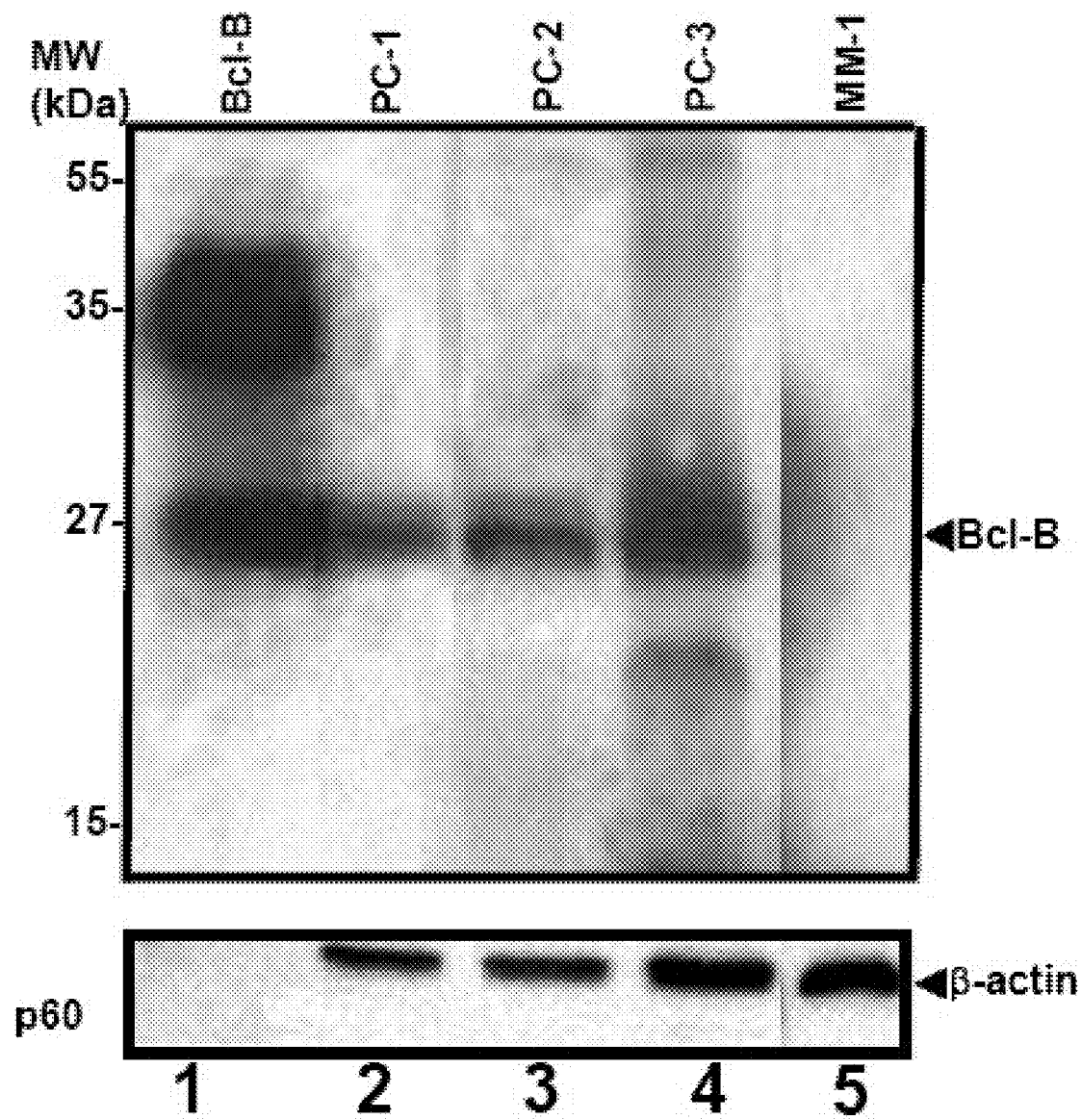
Figure 6C:
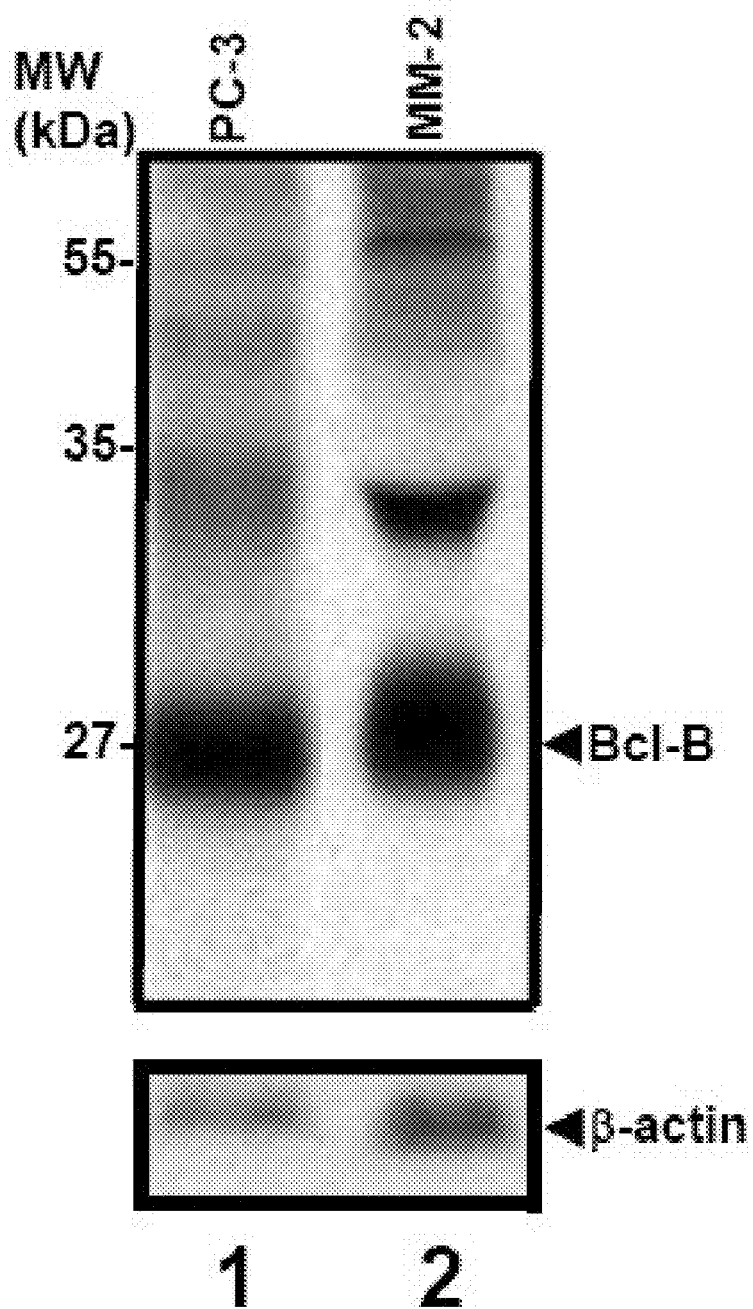

Levels of endogenous Bcl-B varied among tissues and tumor specimens analyzed by immunoblotting. Bcl-B was elevated in NSCLC compared to normal lung in 2 of 2 paired specimens and also higher in a colorectal cancer compared to normal colonic tissue from the same patient (FIG. 1C). In contrast, Bcl-B protein levels were higher in BPH specimen compared to a prostate cancer. Bcl-B protein was also present in 3 of 4 DLCL and 2 of 3 MM specimens tested. Reprobing blot with anti-Hsp60 or anti-β-actin antibodies confirmed equivalent loading of tissue lysates.

b. Immunohistochemical Analysis of Bcl-B Protein Expression in Normal Human Tissues To lay a foundation for assessing Bcl-B expression in cancers, the in vivo patterns of Bcl-B protein expression were first ascertained in normal human tissues by immunohistochemical analysis. The most intense Bcl-B immunoreactivity was found in plasma cells. Strongly stained plasma cells were found in bone marrow, lymphoid tissues, at sites of inflammation, and infiltrating some tumors (FIG. 2). In contrast, erythroid cells, myeloid cells, and megakaryocytes in bone marrow, as well as macrophages, dendritic cells, and most lymphocytes in nodes and extranodular sites of inflammation were Bcl-B negative. Immunoblotting analysis of plasma cells isolated from bone marrow also confirmed the presence of Bcl-B protein (FIG. 6). Moreover, comparisons of immune (FIG. 2A) and preimmune serum (FIG. 2B), as well as preabsorption experiments using GST-Bcl-B (FIG. 2C) or GST-Bcl-$X_L$ fusion proteins (FIG. 2D), confirmed the specificity of plasma cell immunostaining (FIG. 7). The plasma cell phenotype of the Bcl-B-positive cells was also confirmed by two-color immunohistochemical analysis, showing co-expression of Bcl-B with CD 138 (syndecan-1) expressing cells (FIG. 2 I-L). In contrast, the Bcl-B-positive cells were negative for the macrophage marker CD68 in two-color immunostainings.

In addition to plasma cells, Bcl-B also immunolocalized to centroblasts and centrocytes in germinal centers, but not to other types of cells in lymphoid and hematopoietic tissues (FIG. 2E, H), including bone marrow, spleen, nodes, and thymus. The intensity of Bcl-B immunostaining in these lymphocytes however was substantially less than plasma cells (FIG. 2F-G). Among other normal human tissues, Bcl-B expression was detected in hepatocytes, renal tubule epithelium, bronchial and nasopharyngeal epithelium, and type II pneumocytes, as well as cytotrophoblasts in the placenta and some neuronal cells, again with immunointensity much less than observed in plasma cells. In the prostate gland, Bcl-B immunoreactivity was strong in the luminal secretory cells but was absent in basal cells (FIG. 8), thus constituting a pattern of expression opposite of Bcl-2 (Krajewski S, et al. 1995). In all cells examined, the Bcl-B staining pattern was predominantly cytosolic, with a punctate or granular organellar distribution.

c. Bcl-B Protein Expression in Hematopoietic Malignancies

Figure 3:
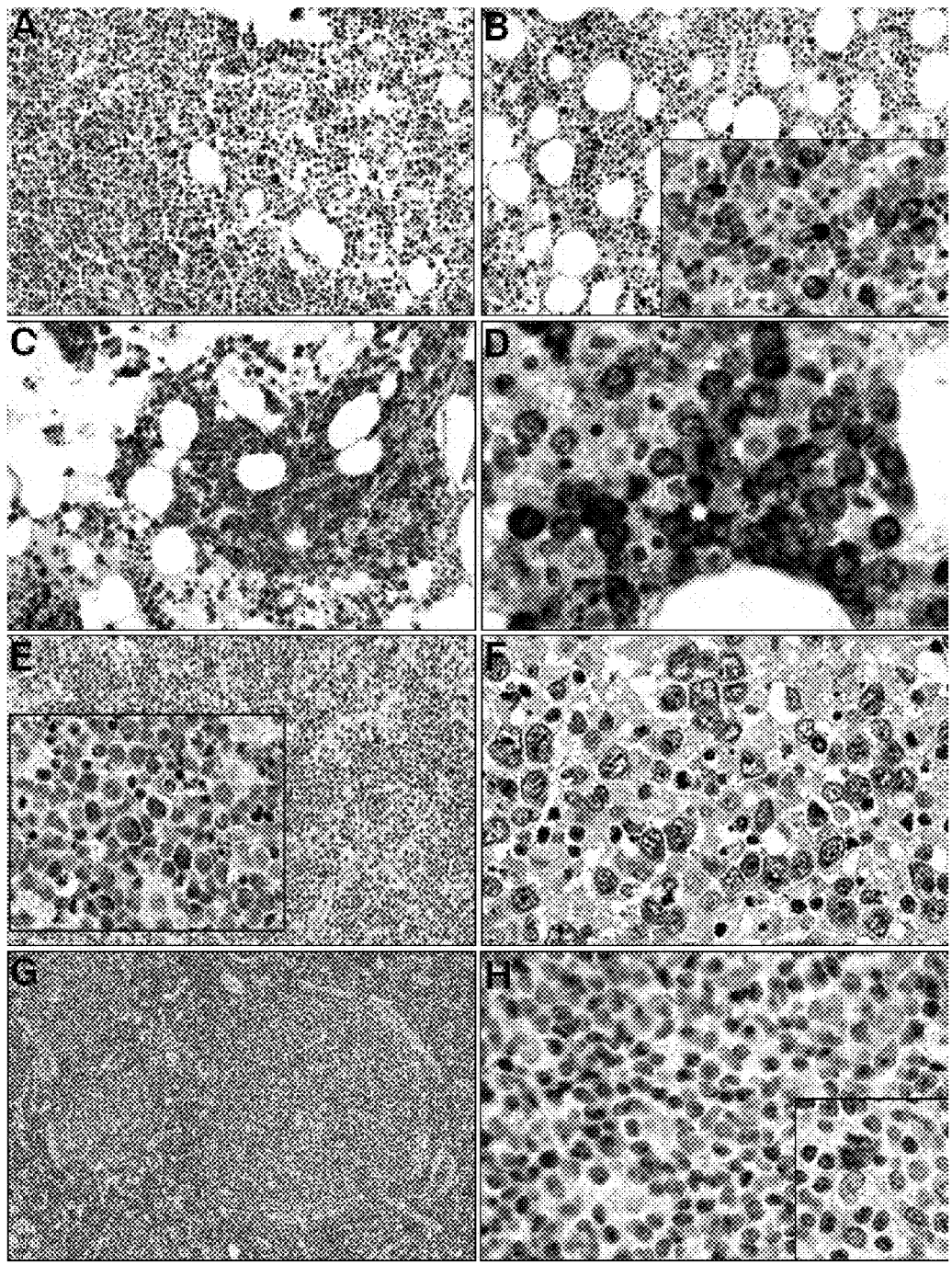
FIGS. 3A-3H show immunohistochemical detection of Bcl-B expression in human hematolymphoid malignancies. Bone marrow biopsies from multiple myeloma patients (A-D), and lymph node specimens from DLBCL (E, F) and FL (G, H) cases were immunostained using Bcl-B antiserum. Original magnifications are 150× (G), 200× (A-C, E), 1000× (D, F, H) and 800-1200× (insets).

Due to the predominant expression of Bcl-B protein in plasma cells, expression of Bcl-B was investigated in plasma cell dyscrasias. Bone marrow biopsies were immunohistochemically evaluated from 165 patients, 114 with symptomatic multiple myeloma (MM), 19 with indolent MM, 13 with monoclonal gammopathy of undetermined significance (MGUS), and 19 with reactive plasmacytosis. Unlike normal plasma cells which appeared to be uniformly Bcl-B-positive, Bcl-B protein was immunolocalized only to a proportion of plasma cells in the 165 specimens of plasma cell dyscrasia, with an average prevalence of 29±2.1% immunopositive cells. Only 16% (26/165) of all tumors showed at least 50% immunopositivity for Bcl-B, with 21 of these high Bcl-B expressors belonging to symptomatic MM (21/114; 18%), 3 to the indolent MM group (3/19; 16%), and 1 each to the MGUS (1/13; 8%) and the reactive plasmacytosis (1/19; 5%) groups. Using 5% cut-off, 30% (49/165) of the plasma cell dyscrasia cases were negative for Bcl-B. FIG. 3 (A-D) illustrates examples of Bcl-B immunostaining in malignant plasma cells. No significant differences in Bcl-B immunoscore values were observed when specimens from MM, MGUS and reactive plasmacytosis cases were compared. Similarly, Bcl-B immunopositivity and immunoscore were comparable in grade 1-3, categorized according to WHO criteria regarding plasma cell content. Bcl-B expression was not significantly associated with patient age, gender, overall survival, or response to therapy in MM.

Lymph node specimens from 48 DLBCL patients were investigated by IHC for Bcl-B expression (FIG. 3E-F). Cases were considered positive if >30% of tumor cells were Bcl-B immunoreactive. Of 48 DLBCL cases, 25 (52%) were Bcl-B immunopositive, using the 30% cut-off that corresponded to the median percentage of Bcl-B positive cells in this cohort. CD 10, Bcl-6, and MUM1 immunostainings were applied to classify the DLBCL cases into GCB and non-GCB groups Hans C P, et al. 2004, using the same cut-off of $\geq$30% Hans C P, et al. 2004. In the investigated patient cohort, 19/48 (40%) were considered GCB and 29 (60%) were classified as non-GCB cases. Both groups contained almost identical proportions of Bcl-B negative and positive cases (47% and 53%, respectively, in the GCB group; 48% and 52% in the non-GCB category). Thus, analysis of the expression of Bcl-B protein in the GCB and non-GCB lymphomas did not reveal significant differences. The Bcl-B immunostaining data also did not correlate with Bcl-2 staining in these DLBCL specimens.

None of the specimens derived from 57 patients with FL contained detectable Bcl-B immunostaining in malignant B-cells (FIG. 3G-H). Positive Bcl-B immunoreactivity in plasma cells observed in these specimens provided an internal staining control.

d. Bcl-B Protein Expression in Solid Tumors

In addition to hematopoietic malignancies, Bcl-B protein expression was investigated in breast, cervical, ovarian, prostate, lung, gastric, and colorectal cancers. The findings provide evidence of alterations in Bcl-B protein expression in several types of solid tumors.

(A) Breast Cancer

TMAs containing specimens derived from 119 stage I-III breast cancer patients were immunostained for Bcl-B. The tissue samples comprised 28 cases of DCIS and 104 ductal, 12 lobular, and 3 mucinous invasive carcinomas. In addition, 12 normal mammary epithelium specimens, excised from surgical margins, were included on the arrays, as well as 4 independent samples of normal mammary gland tissue. Whereas expression of Bcl-B was below the level of detection in normal mammary epithelium, Bcl-B immunostaining was prevalent in 64% of in situ carcinomas and in 89% of invasive cancers (cut-off 10% immunopositive cells), indicating increasing expression with breast cancer progression. Comparison of Bcl-B immunostaining results for transformed vs normal mammary epithelium was highly significant (p<0.0001), using either immunopositivity or immunoscore data (FIGS. 4A-C, 5A).

Figure 5A:
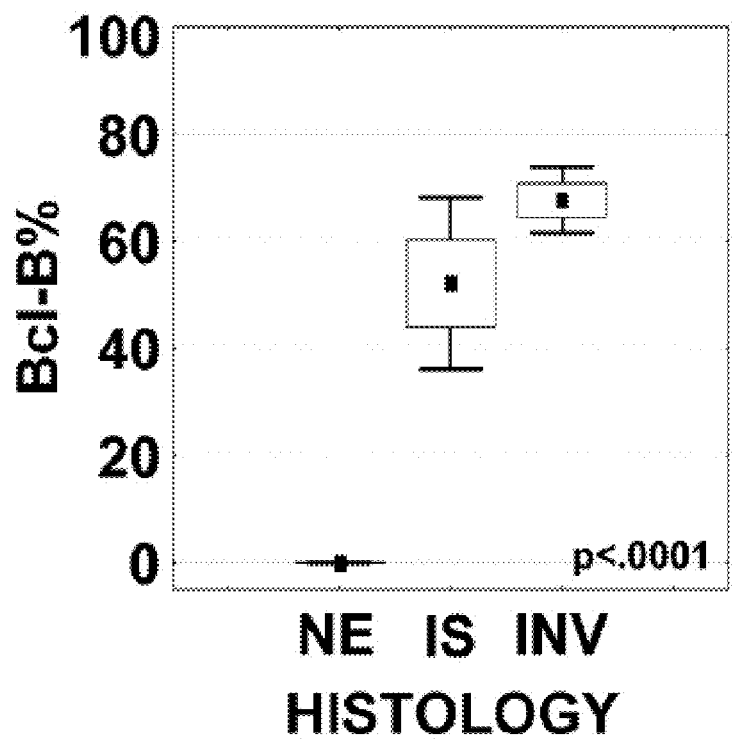
FIGS. 5A-5F show graphic presentation of Bcl-B IHC results in human nonlymphoid malignancies. Box and whisker plots display the distribution of immunopercentage data for Bcl-B in normal mammary epithelium (NE) vs in situ (IS) and invasive (INV) breast carcinoma (panel A), and in normal prostatic epithelium (NE) vs benign prostatic hyperplasia (BPH), prostatic intraepithelial neoplasia (PIN) and prostate cancer (CA) (panel C). Box and whisker plots depict Bcl-B immunoscore data for low vs high grade breast cancers (panel B), for prostate tumors from patients who survived (S) or died from cancer (D) (panel D), and for well (W), moderately (M)
Figure 5B:
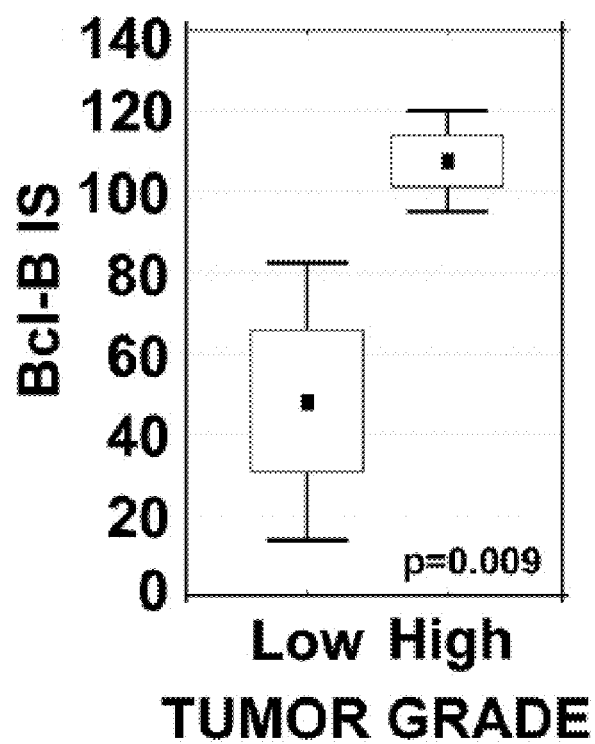

Significantly higher Bcl-B immunostaining was observed in invasive ductal compared to invasive lobular carcinoma (70% vs 47% mean immunopercentage, p=0.03; 108 vs 59 mean immunoscore [IS], p=0.02). Higher Bcl-B immunostaining was associated with more advanced stage of disease (p=0.01 for immunopercentage; p=0.004 for IS), more involved lymph nodes (p=0.04 for IS), and higher histological grade of tumors, with high-grade tumors containing significantly higher levels of Bcl-B protein as determined by immunostaining (70±3.2% vs 42±14.1% immunopositive [p=0.02]); 108±6.4 vs 48±17.6 IS [p=0.009]) (FIG. 5B). Bcl-B elevation in invasive tumors was correlated with higher ER-$\beta$ expression (r=0.42, p<0.0001 for immunopercentage; r=0.37, p<0.0001 for immunoscore) and with lower PR expression (r=−0.22, p=0.02 for immunoscore), but not with ER-$\alpha$ expression. Breast tumors that demonstrated lymphatic vessel invasion (LVI) contained higher levels of Bcl-B protein (p=0.005 for immunopositivity; p=0.0006 for IS).

No correlations were found between Bcl-B expression and patient age, tumor size, or patient survival. In this particular cohort of breast cancer patients, only PR was an independent prognostic factor for overall and disease-free survival in uni- and multivariate analysis (p=0.008; p=0.01, respectively, Cox regression), among all variables assessed (patient age, clinical stage, tumor grade, LVI, ER-α, ER-β, PR, Bcl-B % or IS).

(B) Cervical Cancer

Figure 4:
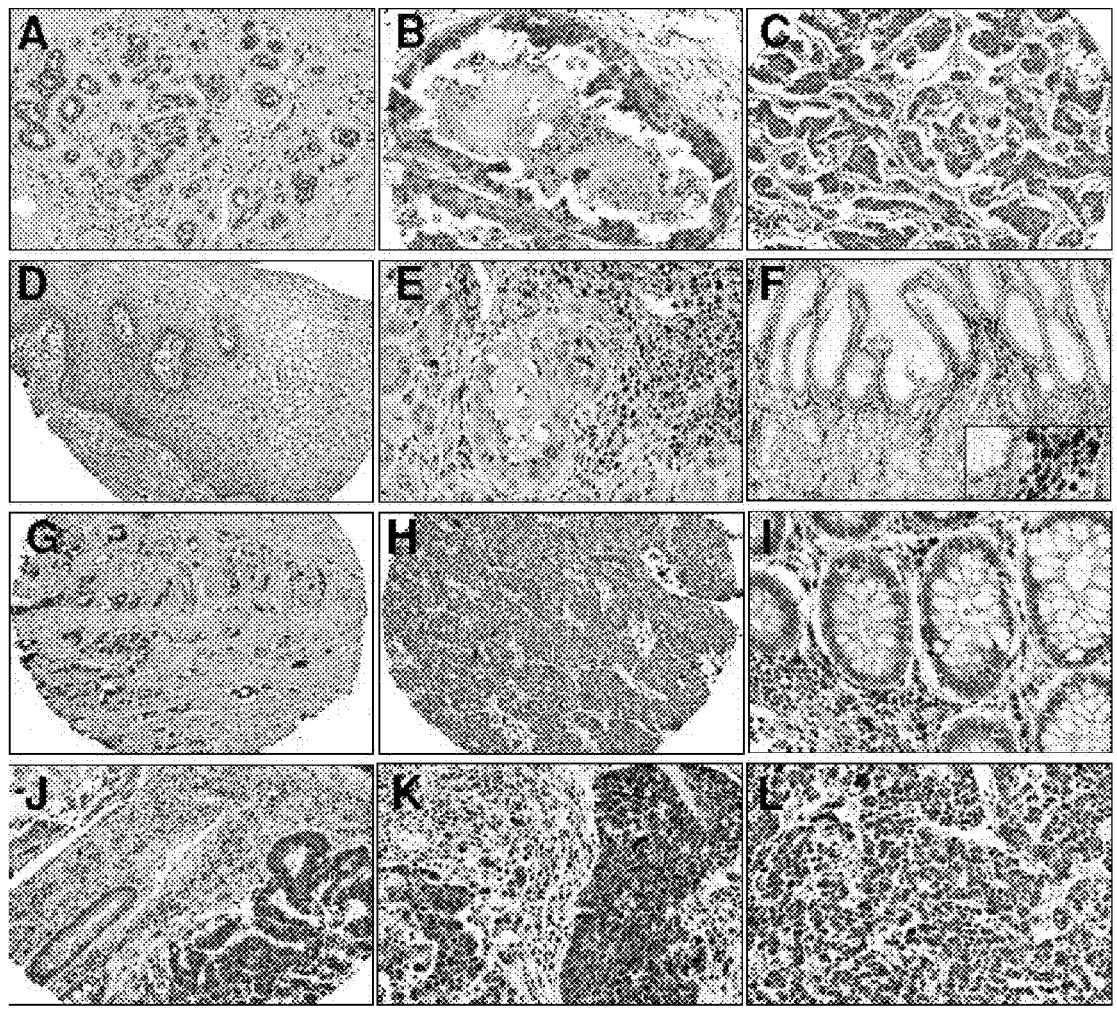
FIGS. 4A-4L show distribution of Bcl-B immunostainings in human nonlymphoid malignancies. Representative Bcl-B immunostaining results are presented for microarrays of (A-C) breast specimens in normal mammary epithelium (A, 60×), DCIS (B, 200×), and ductal adenocarcinoma (C, 60×), (D-E) uterine cervix specimens in normal cervix (D, 60×) and squamous cervical carcinoma (E, 200×), (F-H) gastric specimens in normal gastric epithelium (F, ×100; inset ×300) and gastric cancers (G, H, 60×), (I-J) colon specimens in normal colonic epithelium (I, 200×) and colon cancer (J, 60×), and (K-L) SCLC in primary tumor (K, 200×) and LN metastasis (L, 200×). Note Bcl-B immunopositive plasma cells in normal (F, I) and malignant (E, J-L) tissues.

TMAs containing cervical specimens derived from Asian women diagnosed with cervical intraepithelial neoplasia 1 (CIN1; low-grade squamous intraepithelial lesions; mild dysplasia) (n=47), CIN2 (high-grade squamous intraepithelial lesion; moderate dysplasia) (n=46), CIN3 (high-grade squamous intraepithelial lesion; severe dysplasia—carcinoma in situ) (n=137), and invasive squamous cell carcinoma (n=109) were stained for Bcl-B. Normal cervical epithelium adjacent to the transformed cells was available for each histological entity (n=328) for all patients in the precancerous groups, and 30 of 109 in women diagnosed with invasive cancer. Barely detectable Bcl-B immunostaining was observed in normal epithelium of the exocervix (FIG. 4D) and all stages of the malignant progression (CIN1 to CIN3), indicating that Bcl-B expression is not a characteristic of cervical cancer in this Asian cohort. Strongly stained plasma cells were found infiltrating many cervical tumors, serving as a positive control (FIG. 4E).

(C) Ovarian Cancer

Bcl-B expression was investigated using TMAs containing tissue specimens from 91 ovarian carcinoma patients, and 6 normal ovarian surface epithelium or fallopian tube specimens. The patient cohort comprised 62 individuals with serous carcinomas and 29 cases of non-serous tumors, including mucinous (n=13), endometrioid (n=11), clear cell (n=2), granulose (n=1), dysgerminoma (n=1), and carcinosarcoma (n=1) types.

Low intensity Bcl-B immunostaining was detected in ovarian surface epithelium and normal tubal epithelium, with similar levels of Bcl-B expression found in ovarian cancers. No significant differences in Bcl-B protein levels were noted between the two broad histological categories of ovarian cancer—serous and non-serous. Among these patients, Bcl-B immunostaining did not correlate with patient age, histological grade of tumor, CA 125 serum marker, overall or disease-free survival, or response to therapy. FIGO stages II-IV showed elevated levels of Bcl-B compared to stage I tumors (87±7.6 vs 49±18.4, for IS) but the difference was statistically insignificant. Statistical comparisons performed for a more homogenous cohort of ovarian cancers, namely the 64 serous carcinoma cases, failed to reveal significant associations between Bcl-B expression and the clinical parameters. Thus, Bcl-B over-expression is not a common trait of ovarian cancers.

(D) Prostate Cancer

To characterize the expression of Bcl-B in prostate cancers, TMAs containing patient specimens representing the full range of prostate malignant transformation, including specimens of benign prostatic hyperplasia (BPH; n=38), prostatic intraepithelial neoplasia (PIN; n=11), and prostate adenocarcinoma (n=41) derived from 66 patients were utilized. Gleason score data were available for all tumors, while clinical stage information (T2-T3) (according to International Union against Cancer criteria) was known for 48% of patients. In addition, non-neoplastic prostate epithelium from 14% of cases was available for comparison of protein expression in non-transformed vs neoplastic epithelium.

Figure 5C:
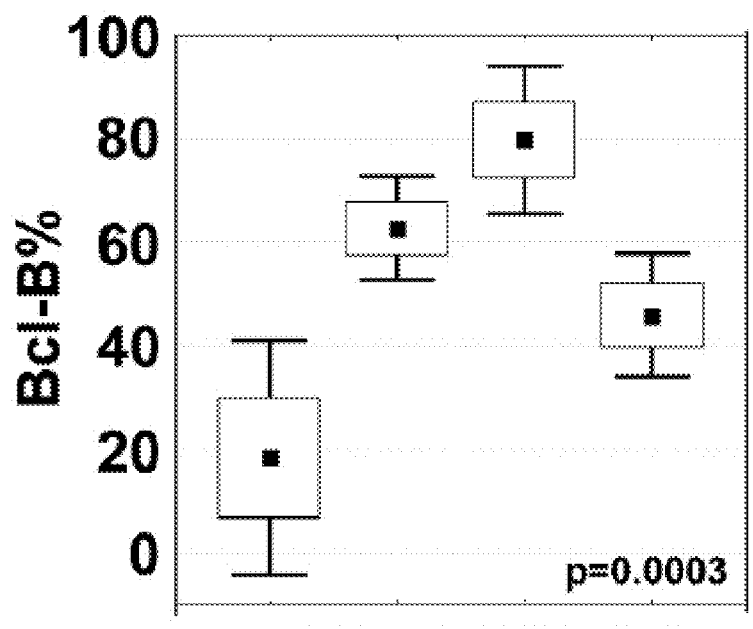
Figure 5D:
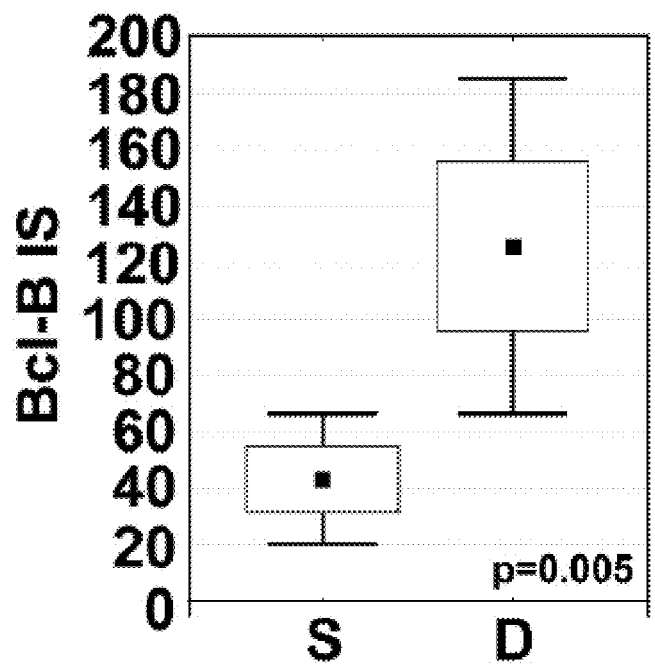

Low expression of Bcl-B was found in the normal prostatic epithelium (mean immunopercentage 18±11.6). Bcl-B expression was markedly increased in BPH (63±5%) and PIN (80±7%) lesions, but less so in the invasive cancers (46±6%) (p=0.0003 for immunopercentage; p=0.01 for IS) (FIG. 5C). Immunohistochemical analysis of specimens revealed higher Bcl-B levels in high-grade tumors (Gleason grade 4) as compared to tumors with Gleason grade 3, however, the difference did not reach the statistical significance. Higher Bcl-B immunoscores correlated with poor clinical outcome, with Bcl-B significantly upregulated in tumors from patients who died from prostate cancer compared to those who survived without relapse during the follow-up period (median follow-up=2.7 years) (65±14% vs 33±9% for immunopositivity [p=0.05]; 126±30 vs 43±18 for IS [p=0.005]) (FIG. 5D). Comparison of preoperational PSA levels suggested that intratumoral Bcl-B is higher in patients with higher PSA levels, but the results did not reach statistical significance.

(E) Gastric Cancer

Archival gastric specimens from 169 Asian patients who underwent surgical resection for localized gastric cancer were analyzed immunohistochemically for Bcl-B protein expression. Bcl-B was expressed in normal gastric surface epithelium, but glands deep within the gastric mucosa were negative for Bcl-B or contained only trace amounts of this protein (FIG. 4F).

Figure 5E:
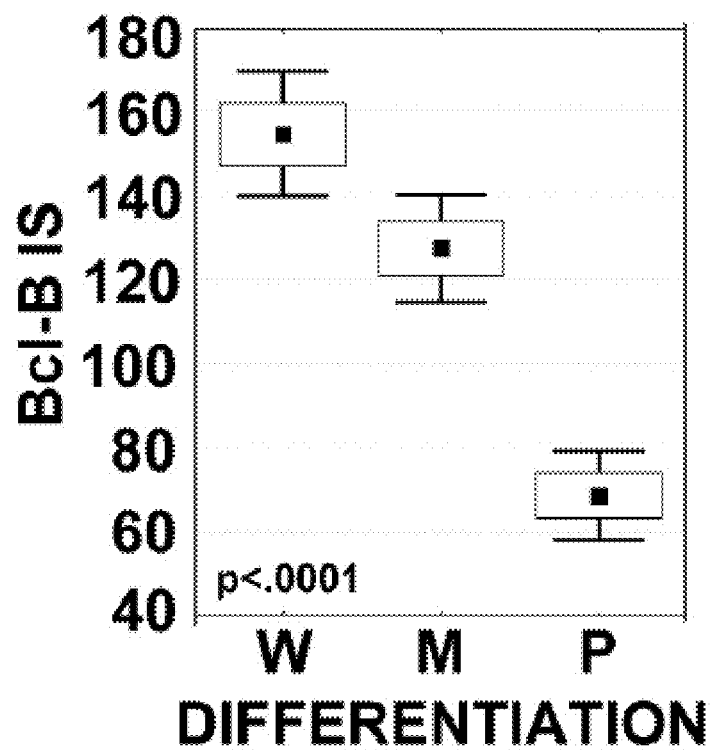

Expression of Bcl-B was prevalent in gastric cancers, with 89% of tumors showing ≧10% immunopositive cells. Bcl-B protein was significantly associated with histological architecture and cellular differentiation of gastric adenocarcinomas, with higher levels of Bcl-B expression in well-differentiated tumors compared to poorly differentiated tumors (90±2.4% vs 52±3% [p<0.0001], and 155±8 vs 69±5 IS [p<0.0001]) (FIG. 5E) and higher Bcl-B levels in intestinal-type (FIG. 4G) compared to diffuse-type cancers (FIG. 4H) (p<0.0001). Similarly, Bcl-B levels in tumors containing signet ring cells were lower than those in non-signet ring cell tumors (43±10.0% vs 75±3% [p<0.0001], and 59±17 vs 118±6 IS [p<0.0001]). Interestingly, tumors with prominent lymphoid infiltration demonstrated higher Bcl-B protein content compared to those that were not infiltrated by lymphocytes (p=0.01 for immunopositivity; p=0.009 for IS).

Although tumors from patients who died from cancer contained slightly lower levels of Bcl-B protein compared to tumors from those who survived (p=0.01 for IS), no significant association with OS or DFS was observed for this patient cohort using Kaplan-Meier survival analysis and log-rank test analysis. Also, Bcl-B expression did not correlate with the clinical stage or mucin content in tumors.

(F) Colorectal Cancer

TMAs were constructed using primary tumor specimens derived from a cohort of 106 Asian patients with stage II CRC, who were treated by surgical resection with curative intent. Of the 106 selected cases, 63 patients survived without recurrence, 7 patients had recurrent disease, and 36 patients died from CRC. Thus, while not an unbiased sequential case series, the survival profile of this cohort closely resembles that of a random population of stage II CRC patients, with 72.5% of individuals alive at 5 yrs. Adjacent normal colonic mucosa was present in 65% of the 106 tumor specimens on the array, permitting side-by-side comparisons of immunostaining results for morphologically normal vs malignant epithelium. In addition, 4 specimens of normal colon derived from individuals who were not diagnosed with colon cancer were stained separately.

Significantly higher Bcl-B protein expression was found in colorectal cancers (FIG. 4J) compared to normal colonic epithelium (FIG. 4I), as assessed by percentage of immunopositive cells (64±5% vs 92±1%) and by immunoscore (82±7 vs 181±6) (p<0.0001; p=0.004, respectively). To explore, if differences in Bcl-B protein expression may correlate with previously identified prognostic features (Elsaleh H.2001), Bcl-B immunostaining was compared with MSI status, anatomical location of tumors, patient gender, and age. In the investigated cohort, higher Bcl-B levels were found in microsatellite stable compared to MSI tumors (p=0.0002 for immunopositivity; p=0.004 for IS), and in the left-sided as compared to right-sided adenocarcinomas (p=0.02 for immunopositivity; p=0.04 for IS). Age and gender were not associated with Bcl-B expression. In univariate analysis, no correlations were observed between OS or DFS and Bcl-B immunostaining data.

Because sections from this same TMA had previously been analyzed by immunohistochemistry for expression of some other Bcl-2-family proteins (Krajewska M, et al. 2005a), Bcl-B immunostaining data was compared with Bcl-2, Bcl-XL, Bax, and Bid. Bcl-B immunostaining in CRCs correlated with $BCl-X_L$ (r=0.43, p<0.0001 for IS) and Bax (r=0.24, p=0.03 for IS), but not with Bcl-2 or Bid.

(G) SCLC

Immunostaining for Bcl-B was performed on SCLC primary tumors obtained by hemithoracotomy from 79 patients with limited-stage disease. The cohort comprised 76% men and 24% women with median age of 57 years, among whom 53% were diagnosed with non-specified SCLC type, 27% with intermediate, 11% mixed intermediate, 5% fusiform/spindle, 3% oat cell, and 1% with polygonal carcinoma. In addition to primary tumors, matching metastatic mediastinal lymph nodes derived from 24 patients in this cohort, were available for investigation.

No significant differences in Bcl-B levels were observed between primary (FIG. 4K) and metastatic tumors (FIG. 4L), as determined by paired t-test. Higher Bcl-B content was found in primary tumors from men (p=0.004 for immunopositivity; p=0.02 for IS) and from older patients (p=0.003 for immunopositivity; p=0.01 for IS). No association was noted between performance status, clinical stage (TNM and UICC stage), tumor size or site (left/right lung) and Bcl-B protein levels in tumors.

Figure 5F:
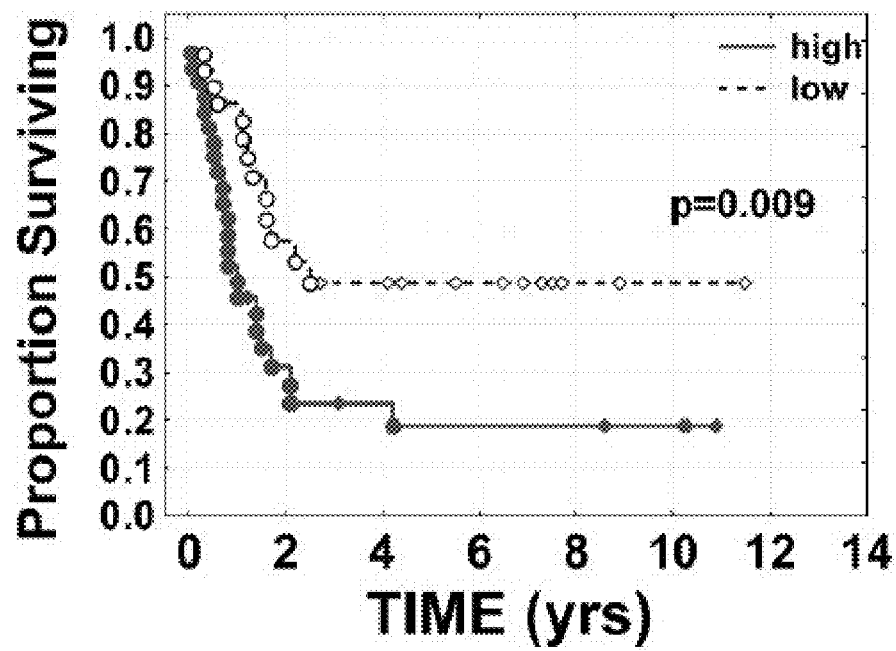

To investigate possible association of Bcl-B expression with clinical outcome, Bcl-B immunopercentage and immunoscore data were dichotomized at the median values into "low" vs "high" expression groups. High Bcl-B prevalence correlated with shorter OS (log-rank test p=0.009; FIG. 5F) and increased relative risk of death due to SCLC (univariate Cox proportional hazards analysis HR 2.4; 95% confidence interval [CI 1.3-4.7]; p=0.008). However, in multivariate Cox analysis, which included patient age, gender, clinical stage, tumor size and size, Bcl-B did not show independent prognostic significance. Bcl-B immunostaining data also did not significantly correlate with time to recurrence after surgery and chemotherapy, though a trend towards higher Bcl-B and shorter time was noted (median 4.9 vs 3.5 years).

(H) NSCLC

TMAs containing specimens from 82 non-small cell lung cancer (NSCLC) patients were immunohistochemically analyzed for Bcl-B protein expression, including 22 adenocarcinomas, 32 squamous cell carcinomas, and 16 large cell carcinomas, and 12 unspecified tumors. Large cell tumors contained relatively low Bcl-B expression (81±15 IS), adenocarcinomas showed intermediate expression (126±20 IS) and squamous cell carcinomas revealed higher Bcl-B content (154±14 IS) (p 0.005). No follow-up data were available for these NSCLC patients.

E. REFERENCES

Bivona T G, Quatela S E, Bodemann B O, et al. PKC regulates a farnesyl-electrostatic switch on K-Ras that promotes its association with Bcl-XL on mitochondria and induces apoptosis. Mol Cell 2006; 21: 481-93.

Chao D T, Korsmeyer S J. Bcl-2 family: regulators of cell death. Annu Rev Immunol 1998; 16: 395-419.

Chauhan D, Velankar M, Brahmandam M, et al. A novel Bcl-2/Bcl-X(L)/Bcl-w inhibitor ABT-737 as therapy in multiple myeloma. Oncogene 2006.

Cheng E, Clem R, Ravi R, et al. Conversion of Bcl-2 to a Bax-like death effector by caspases. Science 1997; 278: 1966-8.

Cheng W C, Berman S B, Ivanovska I, et al. Mitochondrial factors with dual roles in death and survival. Oncogene 2006; 25: 4697-705.

Clem R J, Cheng E H, Karp C L, et al. Modulation of cell death by Bcl-XL through caspase interaction. Proc Natl Acad Sci USA 1998; 95: 554-9.

Elsaleh H. The microsatellite instability phenotype in human colorectal carcinoma: relationship to sex, age, and tumor site. Gastroenterology 2001; 121: 230-1.

Hanahan D, Weinberg R A. The hallmarks of cancer. Cell 2000; 100: 57-70.

Hans C P, Weisenburger D D, Greiner T C, et al. Confirmation of the molecular classification of diffuse large B-cell lymphoma by immunohistochemistry using a tissue microarray. Blood 2004; 103: 275-82.

Inohara N, Gourley T S, Carrio R, et al. Diva, a Bcl-2 homologue that binds directly to Apaf-1 and induces BH3-independent cell death. J Biol Chem 1998; 273: 32479-86.

Ke N, Godzik A, Reed JC. Bcl-B: A novel Bcl-2 family member that differentially binds and regulates Bax and Bak. J Biol Chem 2001; 276: 12481-4.

Krajewska M, Kim H, Kim C, et al. Analysis of apoptosis protein expression in early-stage colorectal cancer suggests opportunities for new prognostic biomarkers. Clin Cancer Res 2005a; 11: 5451-61.

Krajewska M, Kim H, Shin E, et al. Tumor-associated alterations in caspase-14 expression in epithelial malignancies. Clin Cancer Res 2005b; 11: 5462-71.

Krajewska M, Krajewski S, Banares S, et al. Elevated expression of inhibitor of apoptosis proteins in prostate cancer. Clin Cancer Res 2003; 9: 4914-25.

Krajewska M, Olson A H, Mercola D, Reed J C, Krajewski S. Claudin-1 immunohistochemistry for distinguishing malignant from benign epithelial lesions of prostate. Prostate 2007; 67: 907-10.

Krajewska M, Zapata J M, Meinhold-Heerlein I, et al. Expression of Bcl-2 family member Bid in normal and malignant tissues. Neoplasia 2002; 4: 129-40.

Krajewski S, Bodrug S, Krajewska M, et al. Immunohistochemical analysis of Mcl-1 protein in human tissues: differential regulation of Mcl-1 and Bcl-2 protein production suggests a unique role for Mcl-1 in control of programmed cell death in vivo. Am J Pathol 1995; 146: 1309-19.

Krajewski S, Krajewska M, Ellerby L M, et al. Release of caspase-9 from mitochondria during neuronal apoptosis and cerebral ischemia. Proc Natl Acad Sci USA 1999; 96: 5752-7.

Krajewski S, Zapata J M, Reed J C. Detection of multiple antigens on Western blots. Anal Biochem 1996; 236: 221-8.

Le Gouill S, Podar K, Harousseau J L, Anderson KC. Mcl-1 regulation and its role in multiple myeloma. Cell Cycle 2004; 3: 1259-62.

Lin B, Kolluri S K, Lin F, et al. Conversion of Bcl-2 from protector to killer by interaction with nuclear orphan receptor TR3/NGFI-B/Nur77. Cell 2004; 116: 527-40.

Luciano F, Krajewska M, Ortiz-Rubio P, et al. Nur77 converts phenotype of Bcl-B, an antiapoptotic protein expressed in plasma cells and myeloma. Blood 2007; 109: 3849-55.

Manz R A, Moser K, Burmester G R, Radbruch A, Hiepe F. Immunological memory stabilizing autoreactivity. Curr Top Microbiol Immunol 2006; 305: 241-57.

Meinhold-Heerlein I, Stenner-Liewen F, Liewen H, et al. Expression and potential role of Fas-associated phosphatase-1 (FAP-1) in ovarian cancer. Amer J Pathol 2001; 158: 1335-44.

Oancea M, Mani A, Hussein M A, Almasan A. Apoptosis of multiple myeloma. Int Hematol 2004; 80: 224-31.

Radbruch A, Muehlinghaus G, Luger E O, et al. Competence and competition: the challenge of becoming a long-lived plasma cell. Nat Rev Immunol 2006; 6: 741-50.

Reed J C. Mechanisms of apoptosis (Warner/Lambert Award). Amer J Pathol 2000; 157: 1415-30.

Reed J C. Mechanisms of Bcl-2 family protein function and dysfunction in health and disease. Behring Inst Mitt 1996; 97: 72-100.

Ruifrok A C, Johnston D A. Quantification of histochemical staining by color deconvolution. Anal Quant Cytol Histol 2001; 23: 291-9.

Shapiro-Shelef M, Calame K. Regulation of plasma-cell development. Nat Rev Immunol 2005; 5: 230-42.

Shapiro-Shelef M, Lin K I, Savitsky D, Liao J, Calame K. Blimp-1 is required for maintenance of long-lived plasma cells in the bone marrow. J Exp Med 2005; 202: 1471-6.

Song Q, Kuang Y, Dixit V M, Vincenz C. Boo, a novel negative regulator of cell death, interactst with Apaf-1. EMBO 1999; 18: 167-78.

Wang H-G, Reed J C. Mechanisms of Bcl-2 protein function. Histol Histopathol 1998; 13: 521-30.

Went P, Mayer S, Oberholzer M, Dirnhofer S. Plasma cell quantification in bone marrow by computer-assisted image analysis. Histol Histopathol 2006; 21: 951-6.

Zhai D, Jin C, Satterthwait A C, Reed J C. Comparison of chemical inhibitors of antiapoptotic Bcl-2-family proteins. Cell Death Differ 2006; 13: 1419-21.

Zhang H, Holzgreve W, De Geyter C. Bcl2-L-10, a novel anti-apoptotic member of the Bcl-2 family, blocks apoptosis in the mitochondria death pathway but not in the death receptor pathway. Hum Mol Genet 2001; 10: 2329-39.

What is claimed is:

1. A method of selecting a therapy for treating a subject with breast cancer or prostate cancer, comprising examining the expression of Bcl-B in one or more cells of said cancer, wherein a higher amount of Bcl-B expression in the cancer cells or a higher number or percentage of cancer cells with detectable Bcl-B expression as compared to that of non-metastatic reference cells indicates that the selected treatment is adjuvant chemotherapy or hormonal therapy, wherein a lower or equivalent amount of Bcl-B expression in the cancer cells or a lower or equivalent number or percentage of cancer cells with detectable Bcl-B expression as compared to that of non-metastatic reference cells indicates that the selected treatment is surgery, local therapy, or a combination thereof.

2. The method of claim 1, wherein the reference cells comprise healthy cells from the same tissue of the subject as the cancer cells.

3. The method of claim 1, wherein the reference cells comprise non-cancerous cells of same tissue from the subject.

4. The method of claim 1, wherein the reference cells comprise non-cancerous cells of same tissue from one or more unrelated individuals.

5. The method of claim 1, wherein the reference cells comprise non-cancerous cells from the same tissue of the subject as the cancer cells.

6. A method of selecting a therapy for treating a subject with lung cancer, comprising examining the expression of Bcl-B in one or more cells of said cancer, wherein a higher amount of Bcl-B expression in the cancer cells or a higher number or percentage of cancer cells with detectable Bcl-B expression as compared to that of non-metastatic reference cells indicates that the selected treatment is aggressive chemotherapy, investigational drugs, or a combination thereof.

7. The method of claim 6, wherein the reference cells comprise healthy cells from the same tissue of the subject as the cancer cells.

8. The method of claim 6, wherein the reference cells comprise non-cancerous cells of same tissue from the subject.

9. The method of claim 6, wherein the reference cells comprise non-cancerous cells of same tissue from one or more unrelated individuals.

* * * * *